United States Patent [19]
Argiro et al.

[11] Patent Number: 5,986,662
[45] Date of Patent: Nov. 16, 1999

[54] ADVANCED DIAGNOSTIC VIEWER EMPLOYING AUTOMATED PROTOCOL SELECTION FOR VOLUME-RENDERED IMAGING

[75] Inventors: Vincent J. Argiro, Fairfield, Iowa; Andrew M. Weiss, Edina, Minn.; Mark R. Rainbow, Fairfield, Iowa

[73] Assignee: Vital Images, Inc., Minneapolis, Minn.

[21] Appl. No.: 08/731,535

[22] Filed: Oct. 16, 1996

[51] Int. Cl.$^6$ ................................................ G06T 17/00
[52] U.S. Cl. .......................... 345/424; 345/422; 345/425
[58] Field of Search .................................. 345/425, 424, 345/422; 355/973, 974

[56] References Cited

U.S. PATENT DOCUMENTS

| | | | |
|---|---|---|---|
| Re. 35,798 | 5/1998 | Kimura | 345/424 |
| 5,293,313 | 3/1994 | Cecil et al. | 382/131 |
| 5,297,215 | 3/1994 | Yamagishi | 382/131 |
| 5,371,778 | 12/1994 | Yanof et al. | 364/413.22 |
| 5,381,518 | 1/1995 | Drebin et al. | 345/424 |
| 5,452,416 | 9/1995 | Hilton et al. | 395/161 |
| 5,488,952 | 2/1996 | Schoolman | 600/443 |
| 5,493,595 | 2/1996 | Schoolman | 378/41 |
| 5,542,003 | 7/1996 | Wofford | 382/132 |
| 5,544,283 | 8/1996 | Kaufman et al. | 345/424 |
| 5,557,711 | 9/1996 | Malzbender | 345/422 |
| 5,566,279 | 10/1996 | Katayama | 345/419 |
| 5,590,215 | 12/1996 | Allen | 382/128 |
| 5,602,891 | 2/1997 | Pearlman | 378/62 |
| 5,605,153 | 2/1997 | Fujioka et al. | 600/425 |
| 5,630,034 | 5/1997 | Oikawa et al. | 345/424 |
| 5,647,360 | 7/1997 | Bani-Hashemi et al. | 600/425 |
| 5,694,530 | 12/1997 | Goto | 345/419 |
| 5,734,384 | 3/1998 | Yanof et al. | 345/424 |
| 5,737,506 | 4/1998 | McKenna et al. | 345/425 |

FOREIGN PATENT DOCUMENTS

| | | |
|---|---|---|
| 0368425 | 5/1990 | European Pat. Off. . |
| 0635797 | 1/1995 | European Pat. Off. . |
| 94/23375 | 10/1994 | WIPO . |

OTHER PUBLICATIONS

Picker International, Inc., Voxel Q, Basic Operation, pp. 4–1 to 4–10, Aug. 15, 1996.
Picker International, Inc., 4–D Angiography, pp. 16–1 to 16–8, Aug. 15, 1996.
Picker International, Inc., 4–D Angio View–mode, pp. 16–1 to 16–6, Sep. 10, 1997.
Picker International, Inc., epi–Volume, pp. 21–1 to 21–10, Jul. 23, 1996.
Picker International homepage, epi–Volume Product Data, pp. 1–4, <http://www.picker.com>, 1996–98.
V. Argiro, "Seeing in Volume", *PIXEL,* 35, 38–39, (Jul./Aug. 1990).

(List continued on next page.)

*Primary Examiner*—Mark K. Zimmerman
*Assistant Examiner*—Albert K. Lee
*Attorney, Agent, or Firm*—Schwegman, Lundberg, Woessner & Kluth, P.A.

[57] ABSTRACT

A computerized system and method for viewing a set of voxel data on a display device attached to a computer is disclosed. In one embodiment of the invention, the computerized system has a number of different components. A retrieve data set component retrieves the set of voxel data, the set of voxel data having already been acquired in accordance with acquisition parameters of a protocol. A protocol selector component selects the protocol in accordance with the set of voxel data retrieved, the protocol including preset adjustments for the volume-rendering of the data. An image gallery component displays one or more images of the set of voxel data in accordance with the preset adjustments of the protocol. An examination viewer component permits the changing of the preset adjustments of the protocol as to a particular image selected. within the image gallery component. A report generator and viewer component generates a report based on snap shots of images taken within the examination viewer component. A print and post component prints the generated report to a printer operatively coupled to the computer, and/or posts the report as an HTML file to a web browser for retrieval over the Internet or an intranet.

20 Claims, 20 Drawing Sheets

OTHER PUBLICATIONS

V. Argiro, et al., "VOXELS: Data in 3–D", *Byte,* 177–180, 182, (May 1992).

N. Cutner, "The Breakthrough", *Life,* pp. 71–72, 74 (Jun. 1992).

R. A. Drebin et al., "Volume Rendering", *Computer Graphics,* vol. 22, No. 4, pp. 65–74 (Aug. 1988).

K. A. Frenkel, "Volume Rendering", *Communications of the ACM,* vol. 32, No. 4, 426–435, (Apr. 1989).

M. E. Gehr, et al., "The Accuracy of Dental Radiographic Techniques Used for Evaluation of Implant Fixture Placement", *The International Journal of Periodontics & Restorative Dentistry,* vol. 15, No. 3, pp. 269–283, (1995).

A. Kaufman, "Chapter 1: Introduction to Volume Visualization", *IEEE,* pp. 1–18 (1991).

T. Kiely, "Beholding the Brain", *Computer Graphics World,* 2 pgs unnumbered, and pp. 28, 31–32, (Dec. 1991).

A. Kupfer, "New Images of Babies Before Birth", *Fortune,* p. 87, (Aug. 9, 1993).

D. Laur et al., "Hierarchical Splatting: A Progressive Refinement Algorithm for Volume Rendering", *Computer Graphics,* vol. 25, No. 4, pp. 285–288 (Jul. 1991).

M. Levoy, "Volume Rendering: Display of Surfaces from vol. Data", *IEEE Computer Graphics & Applications,* 148–156 (May 1988).

P. LoPiccolo, "The Visible Volume", *Computer Graphics World,* pp. 44–45 (Apr. 1991).

D. P. Mahoney, "International Medicine", *Computer Graphics World,* pp. 47, next page unnumbered, 51, 53–54, (Apr. 1991).

D. P. Mahoney, "Small Worlds", *Computer Graphics World,* 57–58, 61 (Apr. 1991).

G. D. Rubin, et al., "Perspective Volume Rendering of CT and MR Images: Applications for Endoscopic Imaging", Reprinted from *Radiology,* vol. 199, No. 2, 321–330, (May 1996).

M. Snider, "Computer modeling lets physician 'inside' patient", *USA Today,* publication date unknown.

L. Stapleton, "From the Inside Out", *Computer Graphics World,* pp. 89, 91–92, (Apr. 1992).

L. Westover, "Footprint Evaluation for Volume Rendering", *Computer Graphics,* vol. 24, No. 4, pp. 367–376 (Aug. 1990).

J. Wilhelms et al., "A Coherent Projection Approach for Direct Volume Rendering", *Computer Graphics,* vol. 25, No. 4, pp. 275–283 (Jul. 1991).

W. Van Zandt, et al., "A New 'Inlook' on Life", *UNIX Review,* vol. 7, No. 3, pp. 52, 54–57 (Mar. 1989).

W. VanZandt, "Scientific Visualization: One Step in Lab Analysis Workflow", *Advanced Imaging,* pp. 20, 22, and 73 (Feb. 1992).

"Voxel View: Vital Images, Optimizing the Value of Medical Imaging", Brochure : *Vital Images Inc.,* Fairfield, Iowa, (1995).

ADVANCED DIAGNOSTIC VIEWER EMPLOYING AUTOMATED PROTOCOL SELECTION FOR VOLUME-RENDERED IMAGING

FIELD OF THE INVENTION

The present invention relates generally to the viewing of images on a display device coupled to a computer, and more specifically to the viewing of such images that are three-dimensional volume renderings.

BACKGROUND OF THE INVENTION

Because of the increasingly fast processing power of modem-day computers, users have in droves been turning to computers to assist them in the examination and analysis of images of real-world data. For example, within the medical community, radiologists and other professionals who once examined x-rays hung on a light screen use computers to examine images obtained via ultrasound, computed tomography (CT), magnetic resonance (MR), ultrasonography, positron emission tomography (PET) single photon emission computed tomography (SPECT), magnetic source imaging, and other imaging techniques. Countless other imaging techniques will no doubt arise as medical imaging technology evolves.

Each of the above-identified imaging procedures generates volume images, although each relies on a different technology to do so. Thus, CT requires an x-ray source to rapidly rotate around a patient to obtain hundreds of electronically stored pictures of the patient. Conversely, for example, MR requires that radio-frequency waves be emitted to cause hydrogen atoms in the body's water to move and release energy, which is then detected and translated into an image. Because each of these techniques penetrates the body of a patient to obtain data, and because the body is three-dimensional, this data represents a three-dimensional image, or volume. In particular, CT and MR both provide three-dimensional "slices" of the body, which can later be electronically reassembled.

Computer graphics images, such as medical images, have typically, however, been modeled through the use of techniques that are inherently two dimensional in nature to some degree. One such technique is surface-rendering. Surface-rendering has its foundations in geometry-based modeling. For example, surface-rendering of a three-dimensional volume begins with a three-dimensional form of line drawing, a wireframe model, that is comprised of a network of lines and vectors. Surface-rendering replaces this network of lines and vectors with a mesh of polygons.

In the past two decades, significant advances of surface-rendering techniques have led to surface-rendered images having a great deal of realism. The polygonal model can be elaborately shaded to simulate the play of light and shadow on the object to be imaged, endowing each polygon with known or imagined surface properties. This gives the viewer the sense that he or she is looking through a window and into a virtual world.

However, surface-rendering techniques do just and only that—they render surfaces. Therefore, even with an intricately rendered and incredibly realistic surface-rendered image, there is nothing beyond the surface. The model is a hollow shell lacking the solid continuity that exists in the real world. Looking inside the shell reveals nothing.

Real-world, three-dimensional data also resists accurate imaging in accordance with geometry-based modeling techniques in other ways. Conventional geometric graphics techniques start with a simplified, extracted model of the contents of the original three-dimensional data set. The techniques must extract boundaries or surfaces from the data, and decide how to represent them with geometrical primitives (points, lines and polygons)—a process which can introduce distortions. Conventional geometric graphics techniques, therefore, assume a priori that every object within a three-dimensional domain has an already known shape or a shape which can be accurately determined.

However, three-dimensional data may not have clear boundaries that are easily represented with geometrical primitives. Thus, the user viewing such a surface-rendered imaging of the data is not viewing the data itself inasmuch as the user is viewing an interpretation of the data. Furthermore, surface-rendering requires great effort and time if presented with a complex data set, and if a faithful rendering is sought, even if the rendering is accomplished by a powerful computer.

In response to the deficiencies of geometric-based techniques such as surface-rendering, researchers have turned to three-dimensional-based volume-rendering techniques as a more accurate way to render images based on real-world data. Volume-rendering takes a conceptually simpler approach to rendering than does surface-rendering. Rather than overlay surfaces on a complex model of three-dimensional data, volume-rendering assumes that three-dimensional objects are composed of basic volumetric building blocks.

These volumetric building blocks are commonly referred to as voxels. Whereas, by contrast, the well known pixel is a picture element—i.e., a tiny two-dimensional sample of a digital image have a particular location in the plane of a picture defined by two coordinates—a voxel is a sample that exists within a three-dimensional grid, positioned at coordinates x, y, and z. The voxel has a "voxel value," as that value is obtained from real-world scientific or medical instruments. The voxel value may be measured in any of a number of different units, such as housefields, which are well known to those of ordinary skill within the art. For a given voxel value, a transparency value, to indicate its relative opacity vis-a-vis other voxels, as well as a color value, to indicate its color, may also be assigned (for example, in a particular tabling including such mappings).

Using volume-rendering, any three-dimensional volume can be simply divided up into a set of three-dimensional samples, or voxels. Thus, a volume containing an object of interest is dividable into small cubes, each of which contain some piece of the original object. This continuous volume representation is transformable into discrete elements by assigning to each cube a voxel value that characterizes some quality of the object as contained in that cube.

The object is thus summarized by a set of point samples, such that each voxel is associated with a single digitized point in the data set. As compared to mapping boundaries in the case of geometric-based surface-rendering, reconstructing a volume using volume-rendering requires much less effort and is more intuitively and conceptually clear. The original object is reconstructed by the stacking of voxels together in order, so that they accurately represent the original volume.

Although more simple on a conceptual level, and more accurate in providing an image of the data, volume-rendering is nevertheless still complex. A key requisite of volume rendering is the use of the entire voxel data set to create an image. In one method of voxel rendering, called image ordering or ray casting, the volume is positioned behind the picture plane, and a ray is projected perpendicularly from each pixel in the picture plane through the volume behind the pixel. As each ray penetrates the volume, it accumulates the properties of the voxels it passes through and adds them to the corresponding pixel. The properties accumulate more quickly or more slowly depending on the transparency of the voxels.

In another method, called object-order (or compositing or splatting), the voxel values are also combined to produce image pixels for display on a computer screen. The image plane is positioned behind the volume, and each pixel is assigned an initial background value. A ray is projected perpendicularly from the image plane through the volume to the viewer. As the ray encounters each successive layer of voxels, the voxel values are blended into the background, forming the image according to each voxel's interpreted opacity. The image rendered in this method as well depends on the transparency of the voxels.

Due to such variables present in the volume-rendering process, such as transparency as has been described, volume-rendering does not by itself ensure that the resulting image of data is visually realistic or is the image desired by the end user. The volume-rendering must be conducted correctly to ensure that the image is generated accurately. Moreover, different uses of the resulting image are such that the volume-rendering be performed differently from one use to another. For example, the volume-rendering of cardia tissue requires different opacity presets than does the volume-rendering of bone mass.

Furthermore, even within respect to the same use, volume-rendering may be required to be performed differently depending on the application of that use. For example, one physician may be interested in the most dense cardia tissue of a data set, while another physician may be interested in the least dense cardia tissue of the data set. In either case, the volume-rendering is conducted differently to accentuate the desired features of the data. Typically, color is also added to emphasize the desired features.

Unfortunately, however, the end users who can most benefit from the advantages of volume-rendering are not typically volume-rendering computer graphics experts. With respect to images rendered from sets of medical data (such as patient studies), the end user who can most benefit from volume-rendering techniques are physicians, such as radiologists, and technicians. Volume-rendering enables such users to have access to medical images that may display indicia of disease and medical problems otherwise unavailable to these doctors and technicians.

A physician, however, cannot be expected to master the subtleties of volume-rendering as a computer graphics expert may be expected to. Thus, providing physicians with a volume-rendering tool is ineffective if that tool is not easy to use, and does not permit the physician to quickly conduct a volume-rendering of an image of medical data with the correct presets and in the correct manner. Only in this way is volume-rendering of any use to the physician. That is, only if a physician, or other non-expert end user, can easily and quickly conduct a volume-rendering can it be expected that the physician or other non-expert end user will generate a rendered image that is capable of assisting the physician in making a more informed analysis, such as a medical diagnosis.

SUMMARY OF THE INVENTION

The Advanced Diagnostic Viewer (ADV) provides both a two-dimensional and three-dimensional diagnostic environment that permits end users to create volume-rendered images quickly and easily. One embodiment of the invention comprises six components, a retrieve data set component, a protocol selector component, an image gallery component, an examination viewer component, a report generator/viewer component, and a print and post component. The latter four components interact with a set of volume-rendering routines (that is, a volume-rendering engine), although no embodiment of the invention is particularly limited to any given set of routines. The retrieve data set component permits a user to load a previously acquired set of voxel data. The protocol selector component selects a protocol that includes preset adjustments for the volume-rendering of the data, based on the type of data that was loaded via the retrieve data set component. This protocol allows for an initial volume-rendering of the data that is logical in light of the type of data.

The image gallery component displays these initial volume-rendered images of the data, and permits the user to select a different protocol in accordance with which to render the images. The user is also permitted to select a particular image from the gallery of images provided. Within the examination viewer component, the user in more particular is able to refine the view or views of the selected image. The examination viewer component provides the user with exacting controls in the viewing of the image, although also providing different presets of those controls that correspond to particular types of anatomical or other data that is commonly encountered. The examination viewer component also allows the user to fly around and through the data, to obtain the correct view sought. The user is able to select a number of snapshots of such views, or create a video recording of the views. The report generator/viewer component permits the user to assemble these views into a cogent report, and to further annotate the images. Within the print and post component, the user is able to then print the report, or post it as an HTML document on a world-wide web site accessible through an intranet or the Internet.

In this manner, the invention provides the non-expert end user with an environment to easily and accurately generate the desired volume renderings of data. The protocol selector component automatically selects a protocol that guides the initial volume-rendering of the data, so that the user begins with a useful starting point in obtaining the desired volume-renderings. The examination viewer component, while providing a myriad of controls to permit a user to obtain the exact volume-rendering desired, also provides a number of different presets of these controls to aid the user in generating the correct volume-rendering. The user is able to jump among components at any time, such that the entire volume-rendering process is interactive as well.

DETAILED DESCRIPTION OF THE INVENTION

INVENTION OVERVIEW AND HARDWARE DESCRIPTION

The Advanced Diagnostic Viewer (ADV) is a three-dimensional medical imaging workstation, comprised of software running on general-purpose, high-performance three-dimensional graphics hardware. The invention provides both a two-dimensional and a three-dimensional environment in which to view voluminous data organized into a plurality of voxels, each voxel having at least a voxel value. One particular embodiment of the invention provides a diagnostic environment for medical professionals such as radiologists. This embodiment permits such professionals to view volume data that has been captured through computed tomography (CT) and Magnetic Resonance Imaging (MRI) scanning, in both two and three dimensions. It provides an interactive environment to allow the medical professionals to adjust medical images derived from patent studies quickly and simply, and to create diagnostic reports such as radiology reports based thereon.

Figure 1:
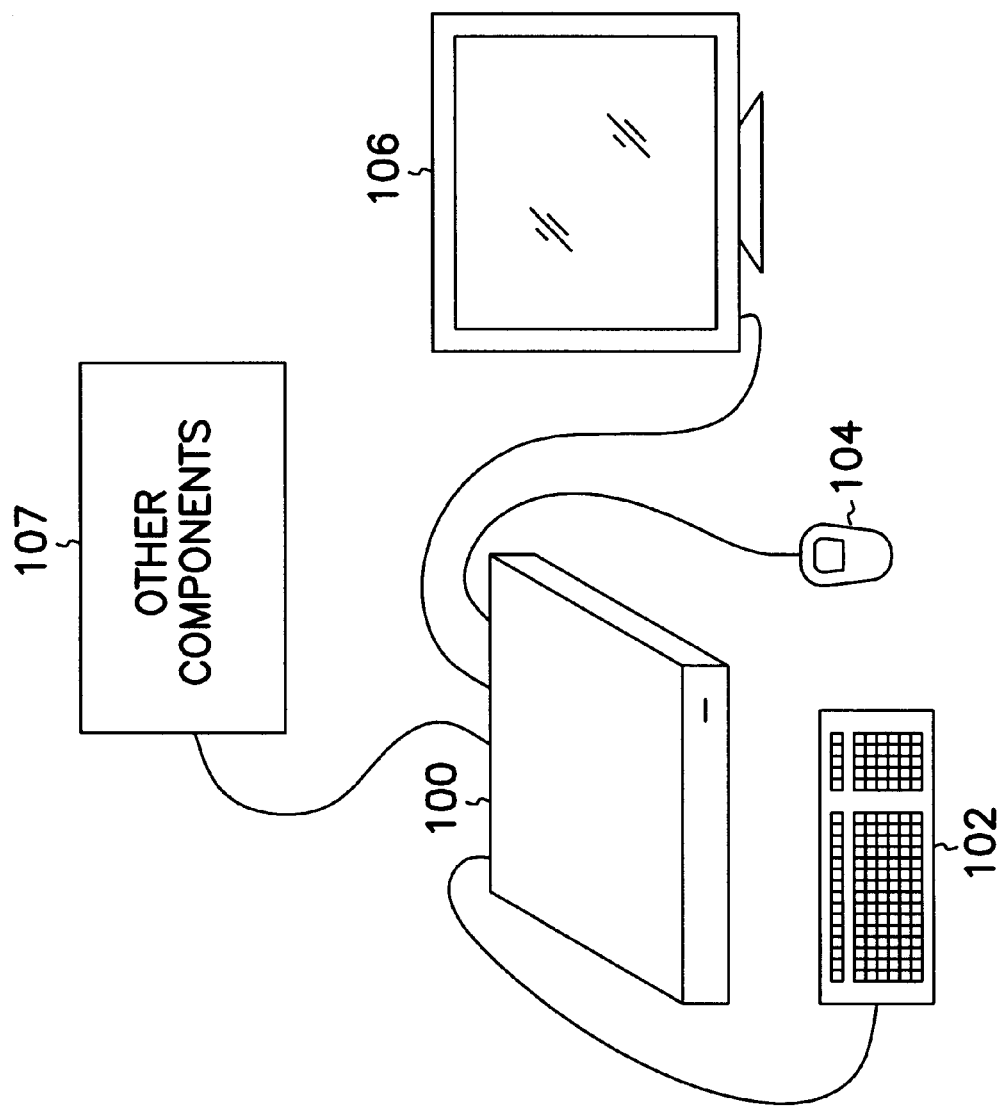
FIG. 1 is a diagram of a typical computer hardware configuration in conjunction with which an embodiment of the present invention is implemented.

The invention is not limited to any particular type of general-purpose, high-performance three-dimensional graphics hardware. A typical example of such hardware, however, is shown in FIG. 1. The hardware shown in FIG. 1 includes computer 100, keyboard 102, pointing device 104, display device 106, and other components 107 (represented by a block diagram). Computer 100 is in one embodiment UNIX compatible. More particularly, computer 100 in one embodiment is a Silicon Graphics, Inc. (SGI) workstation running in an OSF/Motif window environment, with a graphical user interface. Such SGI workstations include the SGI Indigo2 High IMPACT, the SGI Maximum IMPACT, and the SGI O2, all three of which in one embodiment run the SGI Irix 6.2 operating system, in which case the embodiment is based on the OpenGL graphics library, and uses the Viewkit class library. The invention is not limited, however, to any particular computer 100. So long as the computer can sufficiently accommodate high-performance three-dimensional graphics capability, as herein described, the computer is amenable to an embodiment of the present invention.

As shown in FIG. 1, pointing device 14 is a mouse, although the invention is not limited to any particular pointing device. For example, pointing device 104 may also be a point stick, trackball, or a touch pad. The pointing device typically has three buttons, although no embodiment of the invention is so particularly limited. As described herein, clicking, selecting, pressing, or holding, etc., of a pointing device button (such as a mouse button) refers to the clicking, selecting, pressing, or holding, etc., of the left button if there is more than one button on the pointing device.

In one embodiment of the invention, an additional pointing device (viz., part of other components 107 as shown in FIG. 1) is also coupled to computer 100. This additional pointing device is a three-dimensional controller, which allows a user of the invention easy control of the fly through feature of embodiments of the invention. One such pointing device is the Spacetec IMC SpaceBall 3003. Display device 106 can be any of a number of different devices, but in one embodiment of the invention is a computer monitor having a cathode ray tube (CRT). In the embodiment of the invention where computer 100 is an SGI workstation, display device 106 is a twenty-one inch monitor capable of displaying twenty-four-bit color graphics, and having a resolution of 1280×1024 pixels. Furthermore, other components 107 may in varying embodiments of the invention include a video cassette recorder, or a printer. Computer 100 may also have the capability of hooking up to a network (such as a DICOM network), may having Internet or intranet capability, or have access to a DICOM server Each of these is well known to those skilled in the art.

Not shown in FIG. 1 is that computer 100 typically includes a central-processing unit (CPU), a random-access memory (RAM), and a read-only memory (ROM). The CPU, RAM, and ROM may be of any type; no embodiment of the invention is particularly limited. In the embodiment of the invention where computer 100 is an SGI workstation, the CPU is a MIPS R10000, and there are typically one-hundred-twenty-eight megabytes of RAM. Also not shown in FIG. 1 is that computer 100 also usually comprises a fixed storage device such as a hard disk drive, and a removable storage device such as a tape cartridge drive or floppy disk drive. Conversely, such components may be external components to computer 100, in which case they are a part of other components 107. The tape cartridge drive in one embodiment is compatible with a General Electric Genesis tape archive format. No embodiment of the invention is also limited as to the programming language by which the software is implemented. However, in one embodiment, the language is the object-oriented programming language C++.

The invention provides an environment in which volume data comprised of voxels is displayed. No embodiment of the invention is limited as to what this volume data represents. In one embodiment of the invention, the volume data (voxel data) represents medical images of various parts of the human body, as scanned in from a medical imaging device. One embodiment of the invention is specifically described from hereinafter as relating to the viewing of volume-related medical images; however, it should be understood to and appreciated by those of ordinary skill within the art that no embodiment of the invention is so limited.

Figure 2:
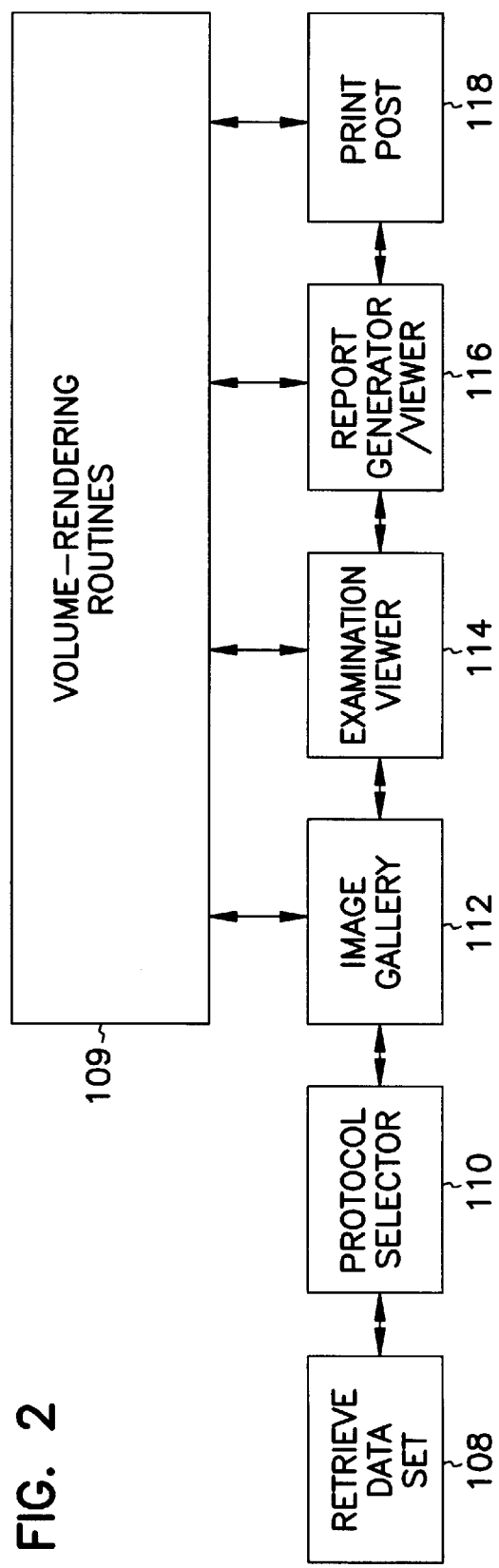
FIG. 2 is a block diagram illustrating the general order of work flow in accordance with an embodiment of the present invention.

Referring now to FIG. 2, the general work flow of the user interface is shown as a block diagram. The ordering of the work flow permits a user to, inter alia, quickly retrieve data such as ultrasound, CT or MRI data over a network, such as that of a hospital; view a gallery of two-dimensional and three-dimensional preview images; select one of the preview images, and fly through or around a three-dimensional image selected; make a diagnosis, take a snapshot of selected images, and create a multimedia report thereof; and, print and post the patient report to an Internet server, to provide instant access to the user. The general work flow comprises six interacting components, as shown in FIG. 2: retrieve data set component 108, protocol selector component 110, image gallery component 112, examination viewer component 114, report generator/viewer component 116, and print and post component 118. Each of these is described hereafter in turn.

Also shown in FIG. 2 is volume-rendering routines 109, which is accessed by and provides data to each of components 112, 114, 116 and 118. Volume-rendering routines 109 contains the routines by which image data acquired from a scanning device is translated into a graphical image viewable on a display device, as modified within any of components 112, 114, 116 and 118. No embodiment of the invention is limited to any particular set of volume-rendering routines 109. As has been described, such volume-rendering routines are well known to those skilled in the art.

RETRIEVE DATA SET COMPONENT

Figure 3:
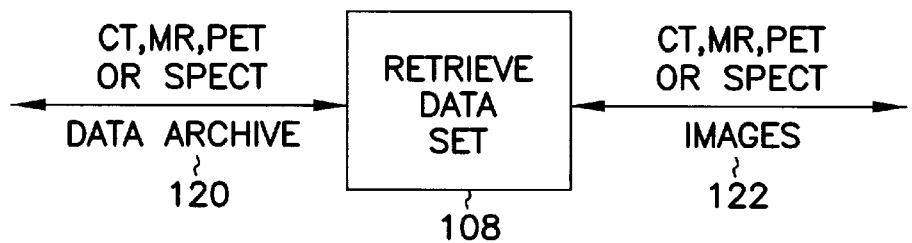
FIG. 3 is a block diagram showing in more particular the retrieve data component of FIG. 2.

Referring now to FIG. 3, retrieve data set component 108 is shown in more particular. Input 120 to retrieve data set component 108 includes data retrieved from any of a number of data archives, according to the user's choice. Output 122 to retriever data sent component 108 includes the actual voxel data for the images as retrieved from input 120. The data is retrieved over a network, file system, or from removable median Component 108 retrieves CT, MRI, positron emission tomography (PET), or single photon emission computed tomography (SPECT) data, and outputs the selected images as encased within that data. The network, file system or removable media from which the data is retrieved may include a DICOM imaging device or other such work station (which is known as the DICOM push method), a DICOM server (which is known as the query/retrieve method), a DICOM part 10 file (from a file system), a DICOM stream file, a data set from VoxelView® 2.5 with a calibrated load.param file, and a General Electric Genesis-compatible tape cartridge (DAT removable media). Each of these data sources is well known to those of ordinary skill within the art.

Figure 4:
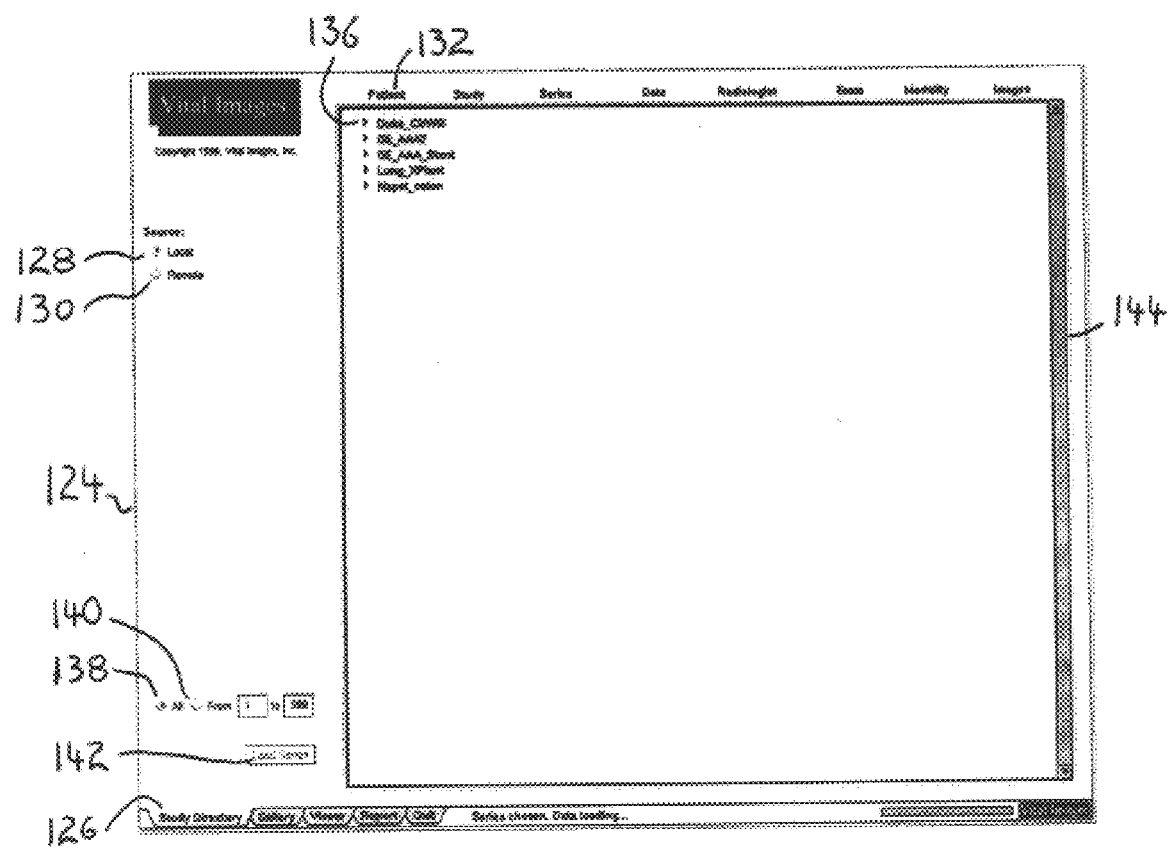
FIG. 4 is a screen shot from an embodiment of the present invention, showing the retrieve data component.

The retrieved data set in one embodiment of the invention corresponds to information regarding a study of a patient. This information is displayed in a window having selectable fields. The user is permitted to select, search or sort the studies by patient name, referring physician name, radiologist, location, date, modality, pathology, data source, protocol, or image report. This is shown in FIG. 4, which is a screen shot from an embodiment of the present invention. Screen shot 124 includes study directory tab 126, local source button 128, remote source button 130, patient header 132, and date sets 134 sorted by patient, where each data set has a corresponding triangle button, such as triangle button 136. In addition, screen shot 124 includes all series selection button 138, range series selection button 140, and load series button 142. Screen shot 124 also includes scroll bar 144, which permits access to all of data sets 134 in the case where there are more data sets than can be listed on the screen at one time.

When one embodiment of the invention first starts, study directory tab 126 is shown. One of source buttons 128 and 130 is pre-selected in accordance with a preferences file; however, the user may override this selection by pressing the desired button. If local source button 128 is selected, the embodiment presents patient data sets 134, as those data sets reside on the local storage device, such as a removable tape cartridge within a tape storage device coupled to the computer on which the software component is running. Conversely, if remote source button 130 is selected, one embodiment presents patient data sets 134, as those data sets reside on the remote storage device, such as a network server compatible with the DICOM protocol.

Figure 5:
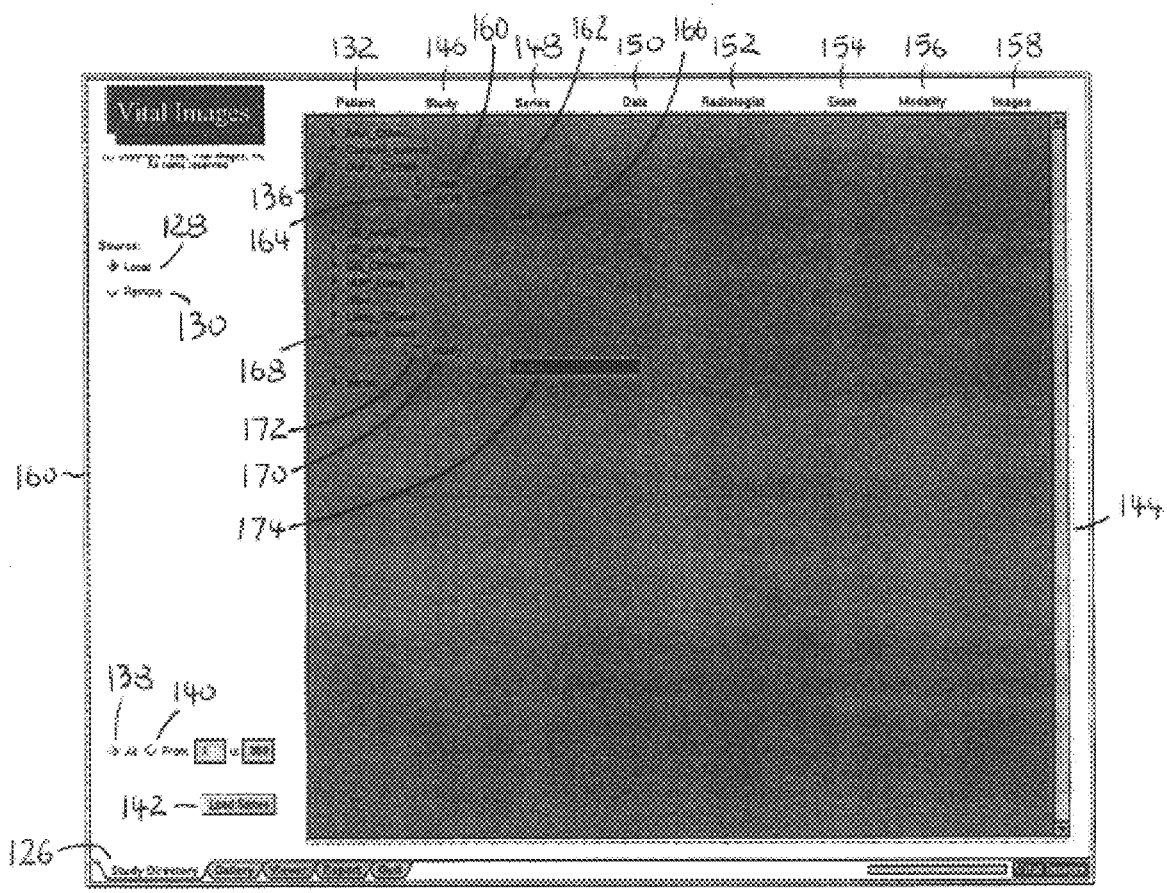
FIG. 5 is another screen shot from an embodiment of the invention, also showing the retrieve data component.

As indicated by patient header 132, data sets 134 are initially identified by patient name. In the example shown in FIG. 4, there are five patient names, Duke_CirWill, GE_AAAw, GE_AAA_Stent, Lung_XPlant, and Napel_ colon. Each patient name has a corresponding triangle button, such as triangle button 136, which is the particularly the corresponding button for the patient study Duke__CirWill. Selecting a triangle button, such as triangle button 136, displays more information regarding the data set for that particular patient. For example, selecting triangle button 136 displays more information regarding the study for the patient Duke__CirWill. This is shown in FIG. 5. Referring now to FIG. 5, screen shot 160 includes study directory tab 126, source buttons 128 and 130, and patient header 132, which are all identical to their counterparts of FIG. 4. Screen shot 160 also includes all series selection button 138, range series selection button 140, and load series button 142, which are also identical to their counterparts of FIG. 4. In addition, screen shot 160 includes scroll bar 144, which is identical to its counterpart of FIG. 4.

There are eight headers for the data sets: patient header 132, study header 146, series header 148, date header 150, radiologist header 152, exam header 154, modality header 156, and images header 158. Each of these headers corresponds to a subject matter of data for the data listed below. As shown in FIG. 5, triangle button 136, corresponding to the patient study named Duke__CirWill, has been selected. Duke__CirWill is a patient because it is positioned within the column headed by patient header 132. Thus, as a result of the selection of triangle button 136, the studies for this patient are shown: studies 160 and 162, where study 160 is labeled exam, and study 162 is labeled 15578. Each of studies 160 and 162 is positioned within the same column as is study header 146. Like the patient data, each of the studies has a corresponding triangle button. As shown in FIG. 5, the triangle button for study 162, triangle button 164, is selected. Therefore, the series for that study are shown, i.e., series 166, labeled Ser8. Series 166 is positioned within the same column as is series header 148.

As also shown in FIG. 5, the triangle button for the patient study labeled Napel__colon, that is, button 168, is also selected. Therefore, study 170 is displayed, labeled study. The triangle button for study 170, triangle button 172, is also selected. Therefore, series 174 is also displayed, labeled series. Series 174 is the series for study 170, which is the study for the patient study labeled Napel__colon. Study 170 is positioned within the column headed by header 146, and series 174 is positioned within the column headed by header 148. As shown in FIG. 5, there are no data, radiologist, exam, modality, or images information shown. Therefore, each of the columns headed by data header 150, radiologist header 152, exam header 154, modality header 156, and images header 158 is empty.

If there is a sufficient number of patient studies within a data set such that not all can be shown on the screen at the same time, and/or if a sufficient number of triangle buttons have been pressed such that not all of the data can be shown on the screen at the same time, then scroll bar 144 permits a user to scroll up or down to view the information desired. Furthermore, the data shown on the screen is limited by all series button 138 and range series button 140. If series button 138 is selected, then all of the series of data within a data set is shown on the screen. Conversely, if series button 140 is selected, then only the series of data as indicated by the user is shown on the screen.

As shown in FIG. 5, series 174 is selected. If load series button 142 is then selected, the voxel data corresponding to series 174 will be selected as the output of study directory tab 126 (i.e., output 122 of retrieve data set component 108 of FIG. 3). A user may also select a particular series by double-clicking it directly, as opposed to selecting the series and pressing load series button 142. In either case, the particular series of voxel data selected is the output of study directory tab 126, and control passes from the retrieve data set component.

As has been described in conjunction with FIG. 4 and FIG. 5, the retrieve data set component (i.e., component 108 as shown in FIG. 2 and FIG. 3) permits a user to select a particular series of voxel data for images for analysis. The screen shots of FIG. 4 and FIG. 5 are from one embodiment of the present invention. Source buttons 128 and 130 permit a user to select the location from which the data will be retrieved. Patient header 132, study header 146, series header 148, date header 150, radiologist header 152, exam header 154, modality header 156, and images header 156 correspond to aspects of the data retrieved from a particular location. By selecting or unselecting triangle buttons for the particular patient studies, a user can determined how much information for a particular patient study is shown on the screen. If there is sufficient information such that not all of the information can be shown on the screen at one time, the user may select scroll bar 144 to scroll up or down within the data. The user may also limit the data by pressing series buttons 138 or 140. Once a user has selected a particular series of voxel data for images to be analyzed, the user double clicks on that series, or otherwise presses load series button 142.

PROTOCOL SELECTOR COMPONENT

Figure 6:
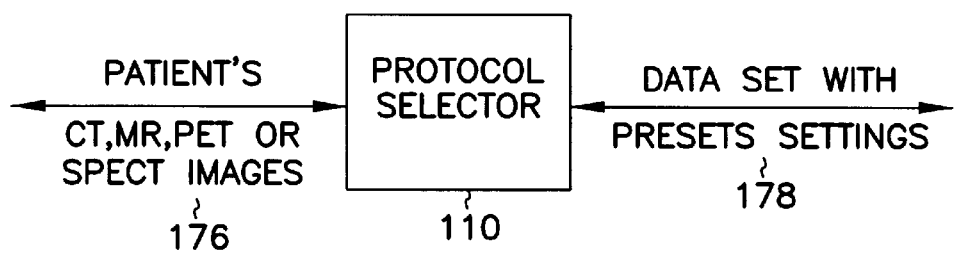
FIG. 6 is a block diagram showing in more particular the protocol selector component of FIG. 2.

Referring now to FIG. 6, protocol selector component 110 is shown in more particular, as compared to as it is shown in FIG. 2. Input 176 to protocol selector component 110 includes the ultrasound, CT, MR, PET, or SPECT voxel data for images as was outputted by retrieve data set component 108 (i.e., output 122 of component 108). Output 178 to protocol selector component 110 includes the voxel data along with presets settings regarding the images to be rendered from the data. Protocol selector component 110 selects a protocol based on input 176, a part of which is the presets settings. In one embodiment of the invention, the protocol is automatically selected based on the DICOM data header, in the case where the data is obtained by retrieve data set component 108 from a DICOM server, network, file, etc. A protocol is defined as a group of preset settings for a patient's data set. The settings and the protocols are generated a priori by clinical testing to determine the most appropriate presets for a particular data set. Protocols span the presets for the viewing of the images within a data set, and in one embodiment also span the presets for performing a specific test to obtain data (i.e., acquisition parameters). However, the latter presets are not required, and no embodiment of the present invention is so limited.

Protocols thus include presets for the visual controls governing the viewing of the volume-rendering of the voxel data, as well as presets for which controls are actually displayed to the user. With respect to the latter, this means that protocols govern the behavior of a user as the user steps through the work flow. That is, as will be described later, if a particular control or set of controls is not useful for viewing of a particular voxel data set, then that control or controls will not be displayed to the user, and the user will not be able to manipulate those controls.

Figure 7:
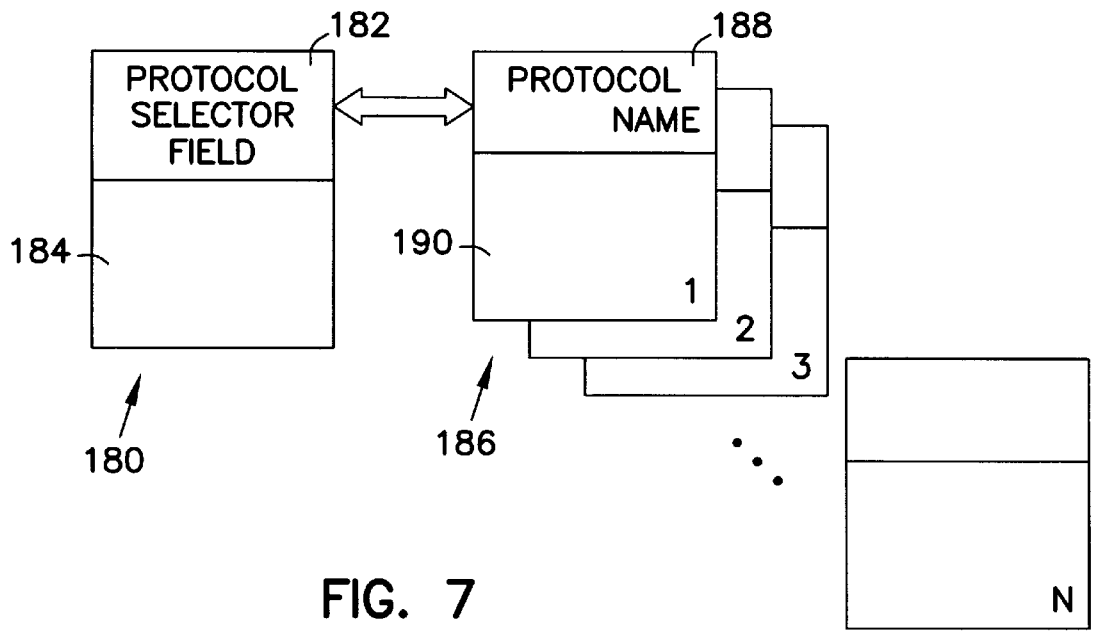
FIG. 7 is a block diagram illustrating the relationship between the input data of FIG. 6 and the protocols that determined the output data of FIG. 6.

Referring now to FIG. 7, a block diagram of the relationship between input data 176 and the protocols determining the output data 176 of protocol selector component 110 is shown. Data 180 is a data set having a field predetermined as protocol selector field 182 and other data components 184. When the data source is from a DICOM server or a DICOM file, etc., an external configuration file specifies which DICOM field is used as protocol selector field 182. When the data source is from a non-DICOM source, the field used as protocol selector field 182 is determined within the data source itself. Protocol selector component 110 uses protocol selector field 182 to match the input data with a protocol for that data.

As shown in FIG. 7, there are 1-N protocols 186, where N is the number of protocols 186. No embodiment of the present invention is limited to a particular number of protocols 186. Each protocol 186 has protocol name 188 and presets 190. No embodiment of the invention is limited to any particular number or type of presets 190. Protocol selector component 110 matches protocol selector field 182 with a protocol name 188 to determine which protocol 186 to use for the particular data 180. The external configuration file specifies which protocol selector fields are to be matched with which protocol names. In the case where the data source is from a non-DICOM source, and the data does not contain information as to a protocol selector field 182, protocol selector component 110 uses a default protocol.

Figure 8:
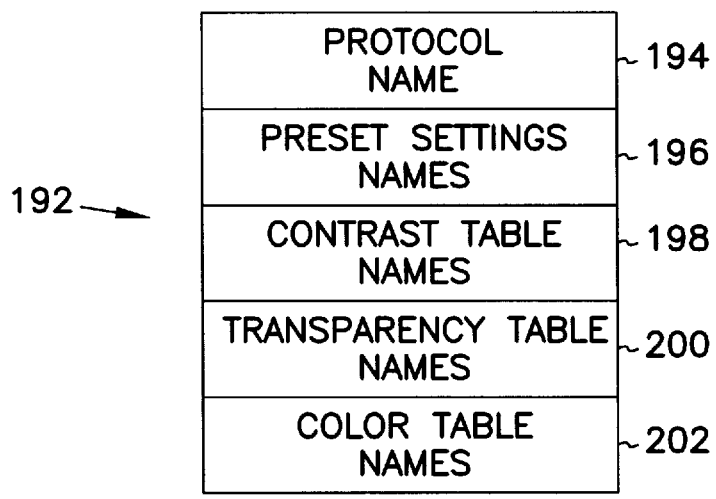
FIG. 8 is a block diagram showing a protocol in accordance with one embodiment of the present invention.

Referring now to FIG. 8, a block diagram of a protocol in accordance with one embodiment of the present invention is shown in more particular. Protocol 192 corresponds to a particular protocol 186 of FIG. 7. Protocol 192 includes protocol name 194, preset settings names 196, contrast table names 198, transparency table names 200, and color table names 202. Protocol name 194 of protocol 192 corresponds to protocol name 188 of protocol 186 of FIG. 7. Preset settings names 196, contrast table names 198, transparency table names 200, and color table names 202 correspond to presets 190 of protocol 186 of FIG. 7. Each of preset settings names 196, contrast table names 198 transparency table names 200, and color table names 202 describes a full set of parameters regarding the initial viewing of an image within the input data set. Not shown in FIG. 8 is that presets 190 may also include scanning parameters for the acquisition of the data that is to be viewed and analyzed. Tables for viewing characteristics include particular mappings of those characteristics to voxel values. For example, a contrast table sets the particular contrast (luminescence) values for voxel values, either individually, by range, or a combination of both.

No embodiment of the invention is limited to any particular set of protocols. However, in one embodiment of the invention, there are protocols titled Circle of Willis, MRA, chest, colonoscopy/bronchoscopy, abdomen, and carotid. As has been described in conjunction with FIG. 7 and FIG. 8, and as specific embodiments have been provided and described, the protocol selector component (i.e., component 110 as shown in FIG. 2 and FIG. 6) facilitates the acquisition and visualization of medical images. A priori, a protocol may specify the parameters surrounding a particular scanning, so that the best possible data can be acquired without undue experimentation on the part of the technician or the radiologist. Ex post, a protocol specifies the presets (e.g., presets 190 of protocol 186 of FIG. 7) regarding the visualization of the data. These presets may include contrast table names, transparency table names, and color table names (e.g., contrast table names 198, transparency table names 200, and color table names 202 of protocol 192 of FIG. 8). This provides the user with an initial view of the images, which can then be modified per the user's desire.

IMAGE GALLERY COMPONENT

Figure 9:
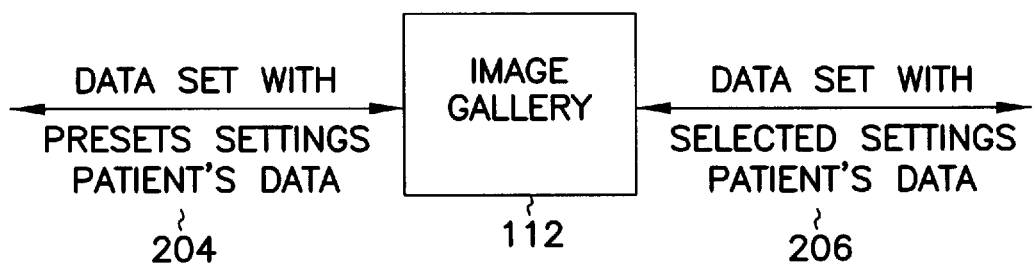
FIG. 9 is a block diagram showing in more particular the image gallery component of FIG. 2.

Referring now to FIG. 9, image gallery component 112 is shown in more particular, as compared to as it is shown in FIG. 2. Input 204 to image gallery component 112 includes the voxel data for images as retrieved and chosen by retrieve data set component 108, along with the preset settings that were determined by protocol selector component 110. That is, input 204 is output 178 of protocol selector component 110. Output 206 to image gallery component 112 includes a data set of one particular image of the data set of input 204, along with the selected settings of that image. Image gallery component 112 displays a number of volume views of the image data within input 204, in accordance with the preset settings specified within input 204. Image gallery component 112 supports multiple views, multiple colorations, and accommodates multiple imaging protocol settings. In one embodiment, one of the views has traditional, black and white radiological settings. From the number of volume views, the user selects an image, and optionally changes the protocol in accordance with which the image is viewed. Output 206 is thus the data for that image, along with the settings dictated by the protocol.

Figure 10:
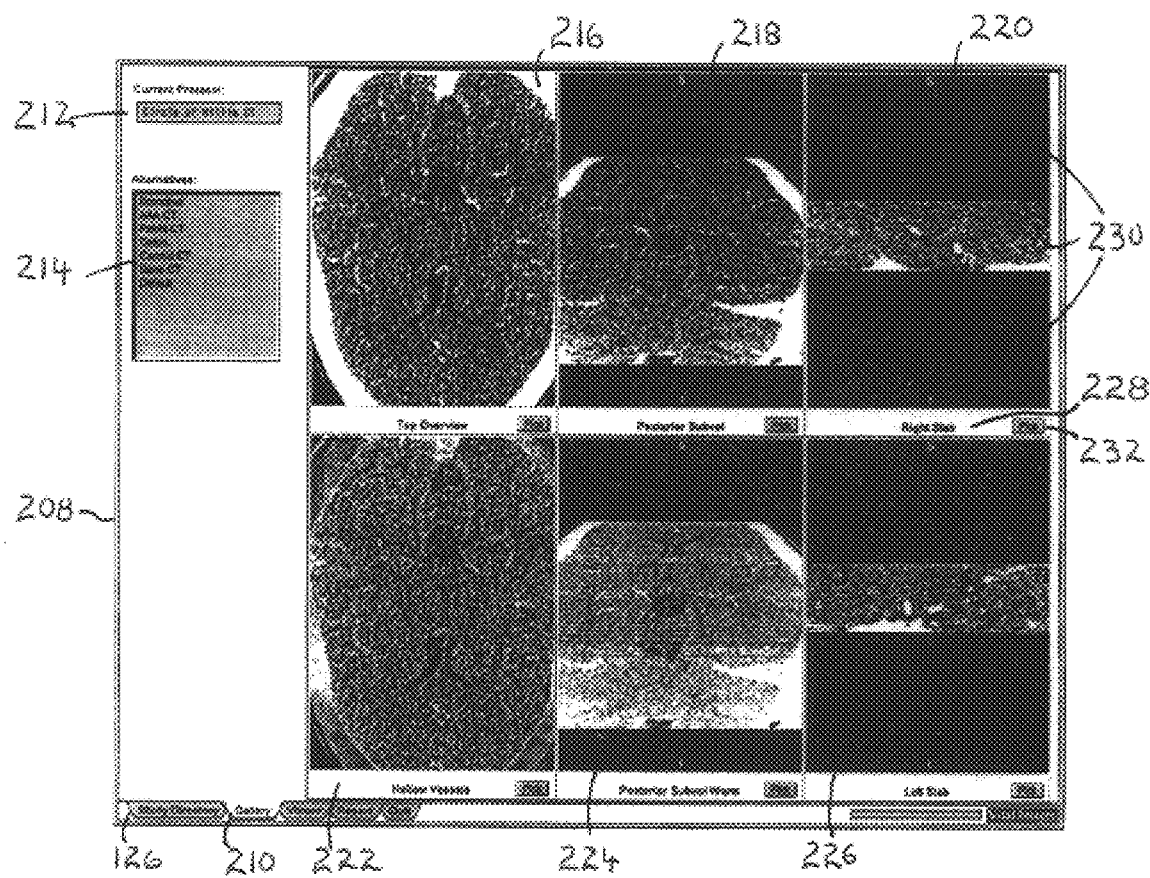
FIG. 10 is a screen shot from an embodiment of the present invention, showing the image gallery component.

As has been already been described, a protocol includes a group of preset viewing settings oriented towards a particular type of study. One embodiment automatically chooses a protocol for display by image gallery component 112, based on the input data. Alternatively, this embodiment uses a generic protocol (i.e., if the protocol selector component is unable to select a protocol based on the input data). Image gallery component 112 thus displays several three-dimensional images using preset variations of the settings for the selected protocol. This is shown in FIG. 10, which is a screen shot from one embodiment of the present invention. Screen shot 208 includes study directory tab 126 (identical to study directory tab 126 as shown in FIG. 4), gallery tab 210, current protocol box 212, protocol alternatives 214, and images 216, 218, 220, 222, 224 and 226. Each image 216, 218, 220, 222, 224 and 226 has a corresponding preset name, four axis indicators, and a pick button. For example, image 220 has preset name 228, axis indicators 230, and pick button 232.

Upon the user selecting a voxel data set via retrieve data set component 108, and protocol selector component 110 selecting a protocol for that data set, image gallery component 112 shows images of that data set in conjunction with the selected protocol. Thus, current protocol 212 initially shows the pre-selected protocol in accordance with protocol selector component 110. Protocol alternatives 214 lists the other protocols through which the image data can be initially viewed. In one embodiment, these protocols include Circle of Willis (CT), Circle of Willis (MR), Carotid (CT), Carotid (MR), Abdominal Aorta (CT), Abdominal Aorta (MR), Heart (CT), Aortic Arch (CT), Pulmonary (CT), Pulmonary (MR), Bronchial (CT), Colon (CT), Spine Disk-Space (MR), Spine (CT), Spine (MR), Pelvis (CT), Extremities (CT), Extremity Vascular (CT), Extremity Vascular (MR), Joint—Knee (MR), Joint—Shoulder (MR), Skull (CT), and Brain (MR). A user, such as a radiologist or a technician, changes the pre-selected protocol by selecting one of the alternatives 214, which then becomes protocol 212.

Each of images 216, 218, 220, 222, 224 and 226 is in accordance with a preset viewing setting of protocol 212. Each protocol 212 can have up to six presets. The protocols and their presets are convenient starting points, but are not necessarily the optimal viewing settings for any particular clinical application. Changing protocol 212 via selection of an alternative protocol 214 thus changes each of images 216, 218, 220, 222, 224 and 226. Each image has a corresponding preset name, four axis indicators, and a pick button. For example, image 220 has preset name 228, axis indicators 230, and pick button 232. Preset name 228 is the name of the preset view shown.

Still referring to FIG. 10, axis indicators 230 show the relative directions of the image, where S indicates superior (front to back), I indicates inferior (back to front), P indicates posterior (bottom to top), and A indicates axial (top to bottom). L and R indicate left and right, respectively, in the case where S is in front, and A is on top. The axis indicators are not identically positioned across the images. That is, S and I may be positioned on the top and the bottom, respectively, for one image, whereas they may be positioned on the left and the right, respectively, for another image. Finally, pick button 232 permits the selection of an image for further viewing, by user depression. Alternatively, the user may double click on an image to select the image. Output 206 of image gallery component 112 is the selected image, as selected by a user pressing the image's corresponding pick button or by double clicking the image, along with the preset information of the selected protocol for that image.

Figure 11:
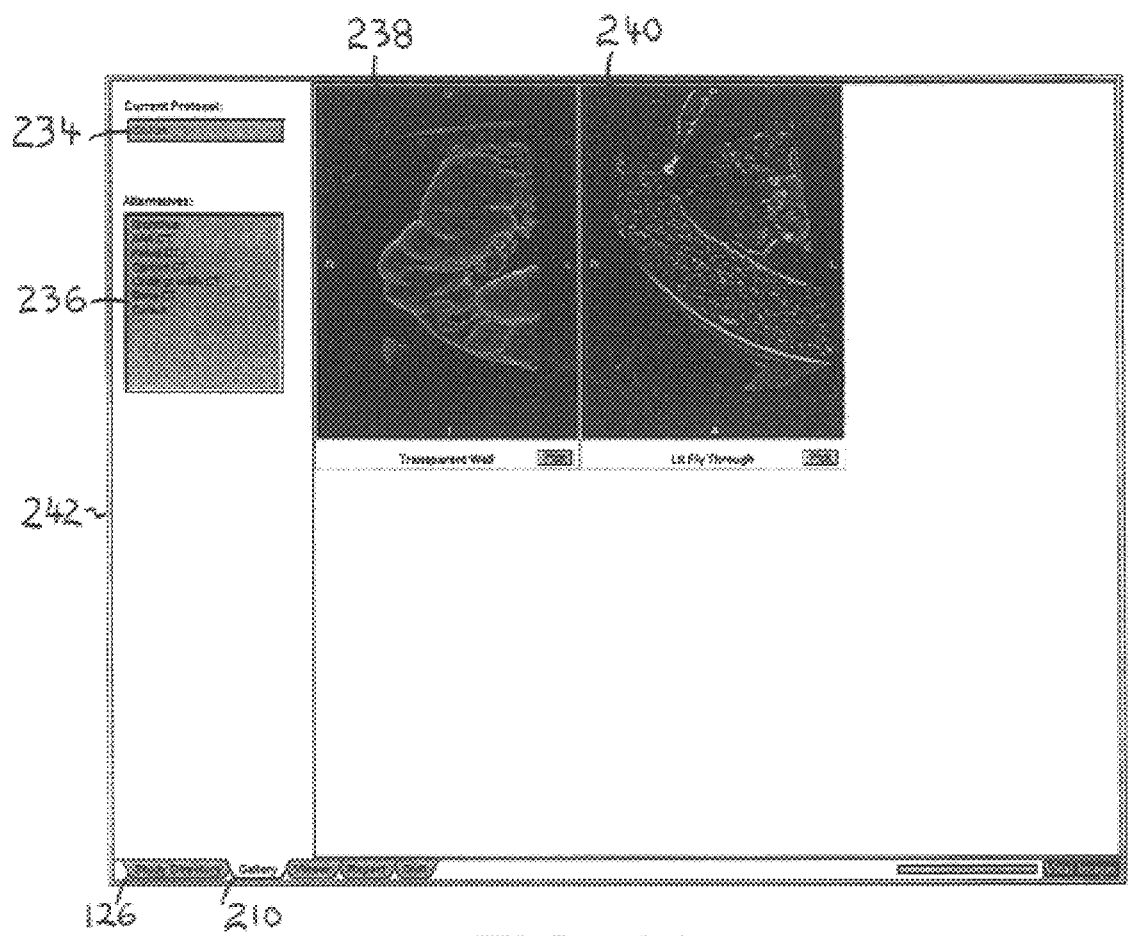
FIG. 11 is another screen shot from an embodiment of the present invention, also showing the image gallery component.

Note that one embodiment of the invention permits a user to go back from image gallery component 112 to retrieve data set component 108 by selecting study directory tab 126 as shown in FIG. 11. That is, this embodiment is not strictly linear, but rather is interactive. If a user changes his or her mind as to the data set to be viewed within image gallery component 112, the user only has to select study directory tab 126 to reselect a particular data set via retrieve data set component 112, as has already been discussed in conjunction with FIG. 3, FIG. 4 and FIG. 5.

As shown in FIG. 10, protocol 212 is the Circle of Willis (CT) protocol. Thus, each of images 216, 218, 220, 222, 224 and 226 is displayed in accordance with this protocol. To provide a contrasting example, reference is now made to FIG. 11. Like screen shot 208 of FIG. 10, screen shot 242 of FIG. 11 is a screen shot of an embodiment of the invention. Screen shot 242 includes study directory tab 126, which is identical to study directory tab 126 of FIG. 10, and gallery tab 210, which is identical to gallery tab 210 of FIG. 10. Screen shot 242 also includes current protocol 234, protocol alternatives 236, and images 238 and 240. Current protocol 234 corresponds to current protocol 212 of FIG. 10, except that in FIG. 11 current protocol 234 is the Colon protocol, whereas in FIG. 10 current protocol 212 is the Circle of Willis CT protocol. Likewise, protocol alternatives 236 corresponds to protocol alternatives 214 of FIG. 10. Note that the list of protocol alternatives shown is not comprehensive with all the protocols that may be available. Thus, for a CT-scanned image, MR-based protocols are not shown in protocol alternatives 236 or protocol alternatives 214.

Still referring to FIG. 11, images 238 and 240 correspond to the preset viewing parameters of the Colon protocol, in the same way as images 216, 218, 220, 222, 224 and 226 of FIG. 10 correspond to the preset viewing parameters of the Circle of Willis CT protocol. The Colon protocol, however, only dictates two sets of preset viewing parameters, and therefore there are only two images, images 238 and 240, whereas the Circle of Willis CT protocol dictates six images, and therefore there are six images in FIG. 10. In addition, like the images of FIG. 10, each of images 238 and 240 has a preset name, axis indicators, and a pick button.

As has been described in conjunction with FIG. 10 and FIG. 11, the image gallery component (i.e., component 112 as shown in FIG. 2 and FIG. 9) permits a user to select a particular image from a series of images for further analysis. The screen shots of FIG. 10 and FIG. 11 are from one embodiment of the present invention. The current protocol is preselected by the protocol selection component, but can be changed by user selection from the protocol alternatives. A user is able to go back from the gallery view to the study directory view by selecting study directory tab 126. A user selects a particular image from the series of images shown for further analysis by selecting the corresponding pick button for the desired image, or by double clicking on the desired image.

EXAMINATION VIEWER COMPONENT
OVERVIEW OF THE EXAMINATION VIEWER COMPONENT

Figure 12:
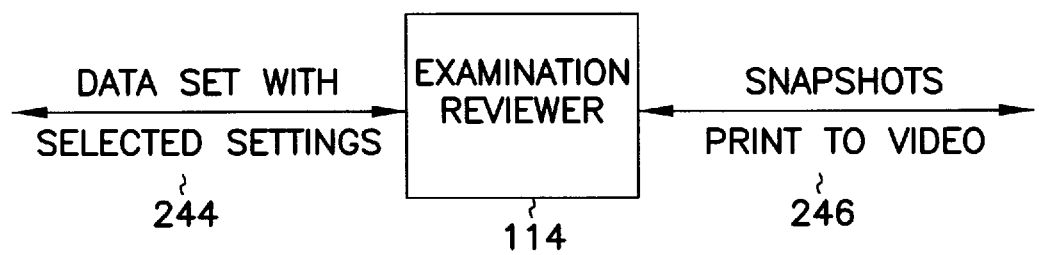
FIG. 12 is a block diagram showing in more particular the examination viewer component of FIG. 2.

Referring now to FIG. 12, examination viewer component 114 is shown in more particular. Input 244 to examination viewer component 114 includes a voxel data set of one particular image of the complete voxel data set as retrieved and chosen by retrieve data set component 108, and as particularly selected within image gallery component 112, along with the selected settings of that image (i.e., from the protocol). That is, input 244 is output 206 of image gallery component 112. Output 246 to examination viewer component 246 includes data for snapshots taken of the particular image selected within image gallery component 112, as viewed from different perspectives and as modified within examination viewer component 114. Output 246 to examination viewer component 246 also includes video output to a video recordation device such as a video-cassette recorder, so that the output can be utilized in an environment not including a computer. Examination viewer component 114 permits display of an image of a patient's data with selected settings by volume view and multiplanar reformatting (MPR) orthogonal or oblique views; by inside view, outside view, and MPR orthogonal or oblique views; and, by volume view only, which is a large three-dimensional rendering. That is, examination viewer component 114 displays different and modifiable views of a selected image data.

Figure 13:
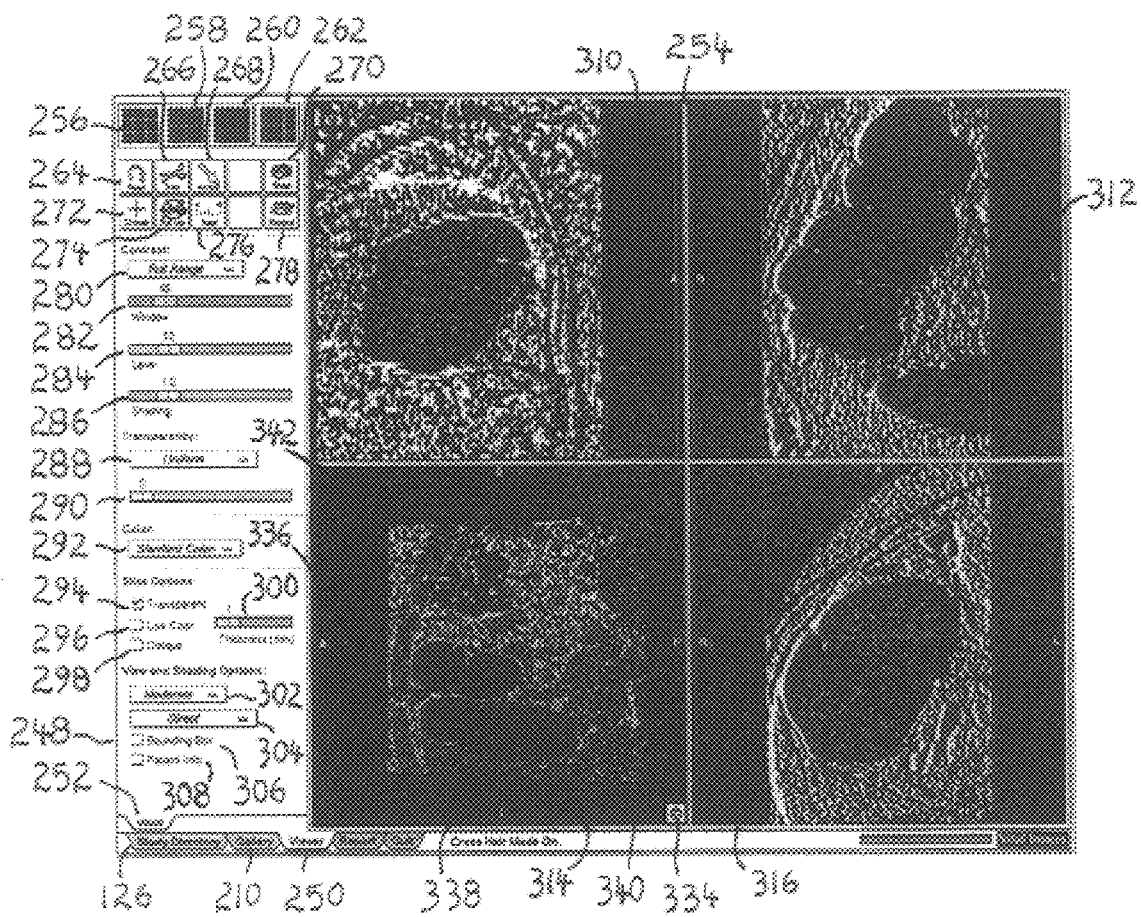
FIG. 13 is a screen shot from an embodiment of the present invention, showing the examination viewer component.

Examination viewer component 114 permits a user to modify an MPR view, by changing slice, toggling between orthogonal and oblique views, panning and zooming, toggling color on and off, changing the transparency of the view, and changing the slab thickness. Furthermore, examination viewer component 114 permits the user to navigate through the different views of an image. The user is able to interactively specify or change the position, the orientation, and the field of view of the "camera" relative to the image data. Examination viewer component 114 permits the user also to visually adjust the views, through a set of tools, and to examine only certain subvolumes of the image data. Examination viewer component 114 provides modeling, measurement and annotation tools to permit the user to better clarify the views. This is all shown by reference to a series of screen shots from one embodiment of the present invention. Referring now to FIG. 13, a screen shot from one embodiment of the present invention is shown. Screen shot 248 includes study directory tab 126 (identical to study directory tab 126 as shown in FIG. 4), gallery tab 210 (identical to gallery tab 210 as shown in FIG. 10), viewer tab 250, visual controls tab 252, and subwindows area 254.

At any time the user can switch to components that have been previously described by selecting either study directory tab 126 or gallery tab 210. If the user realizes, for example, that the incorrect image was selected within the image gallery component, the user can select gallery tab 210 to reselect an image. If the user realizes, for further example, that the incorrect patient study was retrieved within the retrieve data set component, the user can select study directory tab 126 to reretrieve a data set.

Upon the user selecting a particular image within image gallery component 112, examination viewer component 114 shows different views of that image in conjunction with the selected protocol. The settings for each of the controls of controls tab 252 is therefore preset in accordance with the selected protocol for this image. Visual controls tab 252 includes nine-subwindows control 256, four-subwindows control 258, one-subwindow control 260, and five-subwindows control 262. Visual controls tab 252 further includes reset button 264, trim button 266, arrow button 268, snap button 270, cross hair button 272, full volume button 274, ruler button 276, and record button 278. Visual controls tab 252 also includes contrast options menu 280, contrast window slider 282, contrast level slider 284, and contrast shading slider 286. Visual controls tab 252 still further includes transparency menu 288, transparency slider 290, and color menu 292. In addition, visual controls tab 252 includes slice option transparent check box 294, slice option color check box 296, slice option oblique check box 298, and slice option thickness slider 300. Finally, visual controls tab 252 includes orthographic and perspective viewing menu 302, lighting menu 304, view and shading option bounding box check box 306, and view and shading option patient information check box 308. Each of these controls is a part of visual controls tab 252. Further, upon modification of any image within any subwindow by a user, via any of the controls of visual controls tab 252, the user may revert the images back to their initial presentation by selecting reset button 264.

As is shown in FIG. 13, visual controls tab 252 includes various visual controls as has been described. The presence of each of these controls, however, is dictated by the particular protocol selected by the protocol selector component or selected within the image gallery component. For example, for a particular set of voxel data, use of transparency may not be helpful or useful. Therefore, the protocol selected for that set of voxel data may not display the transparency controls, such that the user is not able to change the presets for the transparency of that image. In this manner, one embodiment of the invention permits via its protocol feature the controlling of behavior of the user as the user steps through the embodiment. In addition, the particular protocol dictates the presence of the visual controls tab itself, such that other, similar types of tabs may instead be present, or may be present in addition to the visual controls tab as shown in FIG. 13. No embodiment of the invention is particularly limited to the presence of any particular tab such as visual controls tab 252 of FIG. 13.

Furthermore, various visual controls within visual controls tab 252 have been described hereto as slider controls, or sliders. As described herein, however, the term slider is generic for any sort of similar control. For example, a thumb wheel control, which enables a user to rotate the control to increase or decrease a given value, is also within the term described as a slider. For further example, a box that enables a user to actually enter in a given value via the keyboard is also within the term described as a slider, as those of ordinary skill within the art will well appreciate.

SUBWINDOWS AND DIFFERING VIEWS SHOWN THEREIN

The subwindows of subwindows area 254 contain views of the image in accordance with the preset settings of the controls of visual controls tab 252. Selecting nine-subwindows control 256 displays nine MPR views within subwindows area 254, showing slices that were initially acquired by the scanner. Selecting four-subwindows control 258 displays one three-dimensional image and three two-dimensional MPR views within subwindows area 254. This is specifically shown in FIG. 13. Still referring to FIG. 13, subwindows area 254 comprises subwindows 310, 312, 314 and 316. Subwindow 314 displays the three-dimensional of a view of the image, while subwindows 310, 312 and 316 show corresponding and interrelated orthogonal two-dimensional views.

Figure 14:
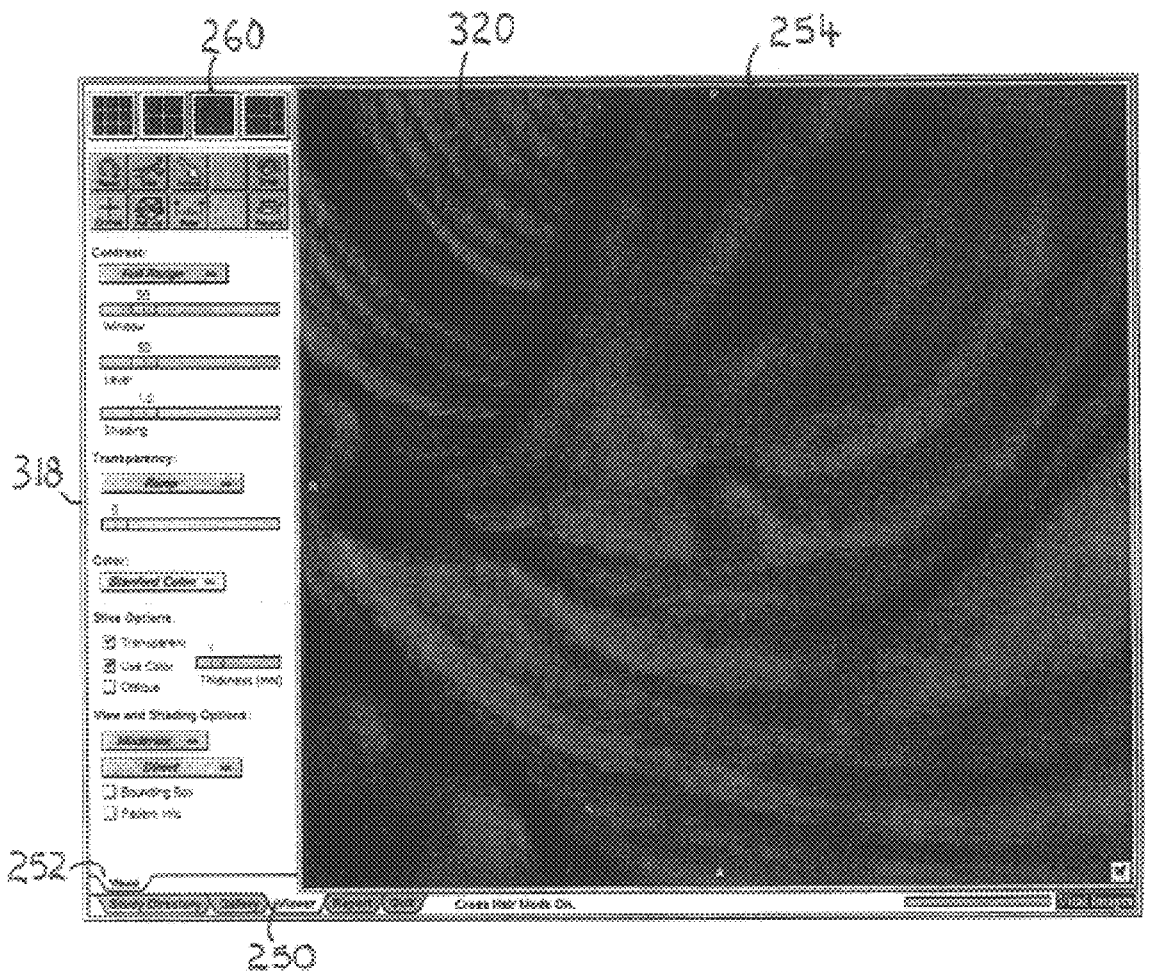
FIG. 14 is another screen shot from an embodiment of the present invention, also showing the examination viewer component, and in particular showing the selection of the one-subwindow control.

Selecting one-subwindow control 260 displays one three-dimensional view of the image. This is specifically shown in FIG. 14, which is a screen shot of one embodiment of the invention. Referring now to FIG. 14, screen shot 318 includes viewer tab 250, visual controls tab 252, subwindow area 254, and one-subwindow control 260, all of which correspond to their counterparts of FIG. 13. Subwindow area 254 of FIG. 14, however, displays only one subwindow, subwindow 320, which is a three-dimensional view of the image.

Figure 15:
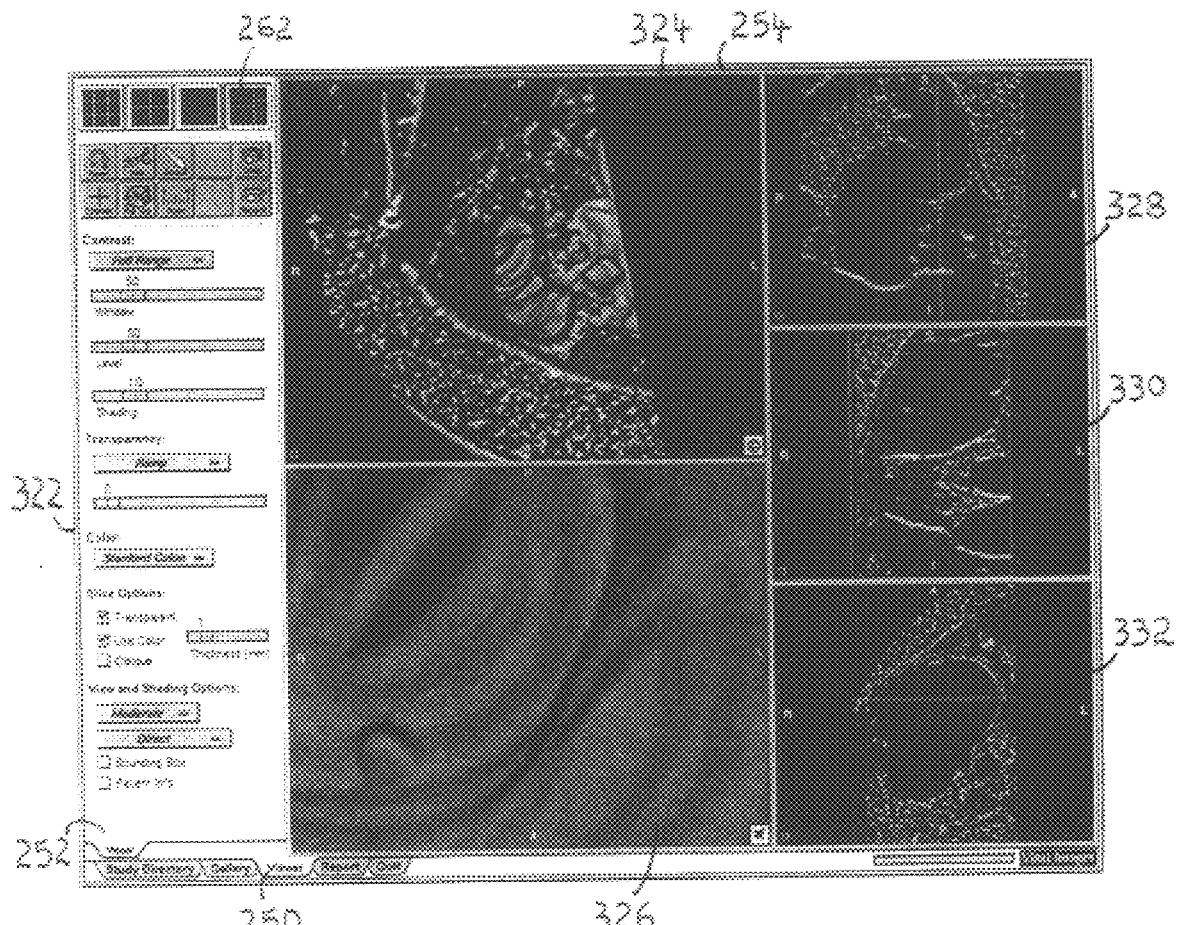
FIG. 15 is another screen shot from an embodiment of the present invention, also showing the examination viewer component, and in particular showing the selection of the five-subwindow control.

Referring back to FIG. 13, selecting five-subwindow control 262 displays two three-dimensional views of the image (an inside view and an outside view), and three two-dimensional MPR views. This is specifically shown in FIG. 15, which is a screen shot of one embodiment of the invention. Referring now to FIG. 15, screen shot 322 includes viewer tab 250, visual controls tab 252, subwindow area 254, and five-subwindows control 262, all of which correspond to their counterparts of FIG. 13. Subwindow area 254 of FIG. 15, however, displays five subwindows, subwindows 324, 326, 328, 330 and 332. Subwindow 324 displays the outside three-dimensional view of the image, and subwindow 326 displays the inside three-dimensional view, while subwindows 328, 330 and 332 show corresponding and interrelated orthogonal two-dimensional views. The selection of a subwindows control 256, 258, 260 or 262 determines to some extent the degree of modification that can be made to the views shown in subwindows area 254. For example, viewing the slices as they were acquired by the scanner (i.e., the ultrasound, CT or MR scanner, as known to those skilled in the art) requires selection of nine-subwindow control 256.

IMAGE ORIENTATION

Referring back to FIG. 13, each of subwindows 310, 312, 314 and 316 show a different orientation of the same image. The orientation of an image is the perspective from which it is viewed. One embodiment permits viewing images from any of the three orthogonal viewing planes: bottom (axial), front (superior), or from the right side (coronal). In addition, this embodiment permits the viewing of images obliquely; for example, from thirty degrees to the left and thirty degrees up.

The orientation of a three-dimensional image, such as the three-dimensional image shown in subwindow 314 of subwindows area 254 of FIG. 13, is modifiable by movement of the mouse in one of two modes, controllable by orientation button 334. Orientation button 334 permits toggling between trackball mode and fly through mode. In trackball mode, moving the mouse while pressing down the left mouse button causes the image shown in subwindow 314 to move (i.e., rotate circularly about an axis). That is, dragging the mouse to the left rotates the image accordingly. In fly through mode, moving a three-dimensional pointing device also coupled to the workstation causes the position from which the image is viewed to change. Fly through mode is best used when navigating inside an image, rather than viewing surfaces of the image. Fly through may be characterized as moving a camera through an image. The current orientation mode of an image is indicated by its corresponding orientation button. When the orientation mode is in trackball mode, the orientation button shows a trackball. This is the state of orientation button 334 in FIG. 13. Alternatively, when the orientation mode is in fly through mode, the orientation button shows a plane.

The actual orientation of an image is indicated by axis labels at each side of a subwindow displaying a view of the image. For example, axis indicators 336, 338, 340 and 342 indicate the actual orientation of the image shown in subwindow 314. As shown in FIG. 13, axis indicator 336, which lies on the left side of subwindow 314, is labeled A, while axis indicator 340, which lies to the right, is labeled P. This means that the anterior to the posterior of the volume is shown left to right. Furthermore, axis indicator 342, which lies on the top side of subwindow 314, is labeled S, while axis indicator 338, which lies to the bottom, is labeled I. This means that the superior (front) to the inferior (back) of the volume is shown top to bottom. By elimination, then, the left side of the volume is the actual viewing plane shown in subwindow 314, while the right side of the volume is not shown except insofar as the volume shown has a particular thickness.

One embodiment also permits the user to activate a bounding box around a volume. A bounding box provides additional orientation cues if the orientation of a three-dimensional image is changed. Furthermore, use of a bounding box is more useful when in trackball mode than when in fly through mode. Activating a bounding box is accomplished by clicking on bounding box check box 306 when the option is not deactivated. Clicking on bounding box check box 306 when the bounding box option is already activated deactivates the option.

Still referring to FIG. 13, the orientation of two-dimensional MPR views, such as those shown in subwindows 310, 312 and 316 of subwindows area 254, are also modifiable. The orientation of a two-dimensional MPR view is determined by the status of oblique check box 298, as well as the orientation of the three-dimensional image shown in subwindow 314. If oblique check box 298 is turned off, the views displayed in subwindows 310, 312 and 316, respectively, are the axial, coronal and sagittal slices (i.e., orthogonal views), regardless of the orientation of the three-dimensional image within subwindow 314. If oblique check box 298 is turned on, however, then the orientation of the two-dimensional views is determined by the orientation of the three-dimensional image. That is, the MPR two-dimensional views represent the slices obtained if the three-dimensional image is cut, in its current orientation, along one of the three planes.

As shown in FIG. 13, the images in subwindows 310, 312 and 314 are orthogonal views because check box 298 is not selected. The image shown in subwindow 310 represents the slice as if the three-dimensional image was cut on the plane of the computer screen (axial). The image of subwindow 312 represents the slice as if the three-dimensional image was cut on the vertical plane that is perpendicular to the computer screen (coronal). The image of subwindow 316 represents the slice as if the three-dimensional image was cut on the horizontal plane that is perpendicular to the computer screen (superior).

One embodiment of the invention uses volume- and surface-rendering techniques that allow for instantaneous changes of the images shown in subwindows 310, 312, 314 and 316. That is, changing the orientation of the image shown in subwindow 314 is nearly and substantially simultaneous to the movement of the mouse or three-dimensional pointing device. Changing the orientation of the three-dimensional image in subwindow 314 while oblique check box 298 is checked also immediately changes the two-dimensional MPR views of subwindows 310, 312 and 314 to reflect the new orientation. If check box 298 is not checked, then changing the orientation of the three-dimensional image within subwindow 314 has no immediate effect. However, if check box 298 is later checked, then the MPR views of subwindows 310, 312 and 316 change to reflect the orientation of the three-dimensional image. When the views of subwindows 310, 312 and 316 change in orientation, their corresponding axis indicators, similar to axis indicators 336, 338, 340 and 342 for the image shown in subwindow 314, also change correspondingly.

Any volume- and surface-rendering techniques can be used in conjunction with an embodiment of the invention, even if those techniques do not provide for instantaneous or otherwise fast rendering. As has been already discussed, any volume- and surface-rendering engine can be used, and such engines are well known to those of ordinary skill within the art.

Discussion of the images shown in subwindows area 254 has been hereto made in conjunction with reference to subwindows 310, 312, 314 and 316 of FIG. 13. This is by way of example only, however, and no embodiment of the invention is meant to be limited to the four-subwindow display shown in FIG. 13. The discussion made in conjunction with the three-dimensional view shown in subwindow 314 of FIG. 13 is also applicable to the three-dimensional view shown in subwindow 320 of FIG. 14, and subwindows 324 and 326 of FIG. 15. Further, the discussion made in conjunction with the two-dimensional views shown in subwindows 310, 312 and 314 of FIG. 13 is also applicable to subwindows 328, 330 and 332 of FIG. 15. That is, the discussion made in conjunction with two-dimensional views as shown in FIG. 13 is applicable to all two-dimensional views of examination viewer component 114, while the discussion made in conjunction with three-dimensional views as shown in FIG. 13 is applicable to all three-dimensional views of examination viewer component 114.

SLICES, MAGNIFICATION AND STEREO VIEWING OF IMAGES

Two-dimensional MPR views, such as those shown in subwindows 310, 312 and 316 of FIG. 13, are defined by three planes: the plane of the computer screen, and the two planes perpendicular to the screen. Each MPR view represents a slice, or cross-section, of a three-dimensional volume, such as that shown in subwindow 314 of FIG. 13. One embodiment permits a user to change from any two-dimensional MPR view from one slice of the volume to any other slice, even if they are not adjacent to one another. Note that the slices do not have to reflect actual slices that were scanned by th imaging device. For example, if the oblique check box (such as box 298 of FIG. 13) is turned on, the MPR views represent three-dimensional slabs created from the data that makes up the volume data set.

Figure 16:
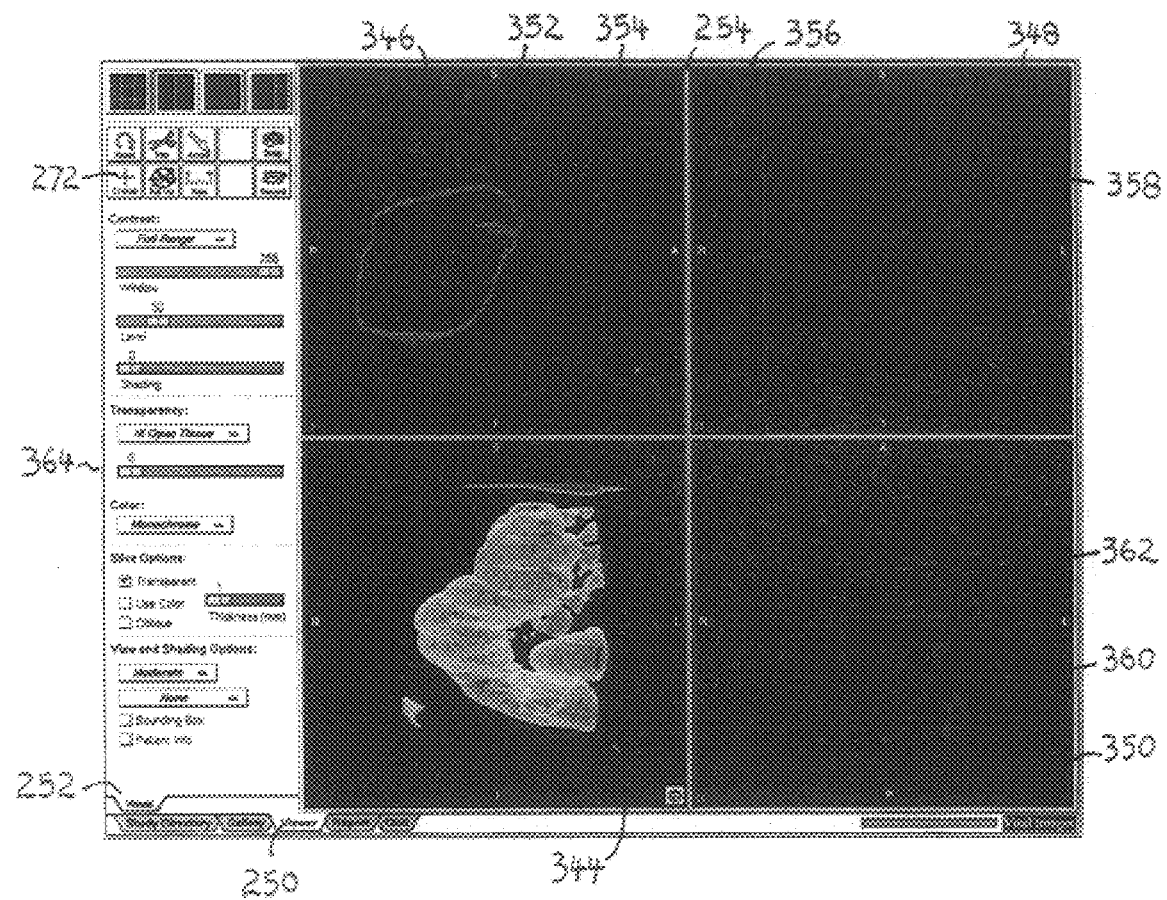
FIG. 16 is another screen shot from an embodiment of the present invention, also showing the examination viewer component, and in particular showing the cross hairs within an MPR two-dimensional view of the image.

Each MPR two-dimensional view has a colored border, with a different color for each view. Therefore, each color identifies a separate plane: the plane of the screen, or one of the two planes perpendicular to the screen. The three MPR views correspond to these three planes. Each MPR view also has cross hairs consisting of vertical and horizontal lines. This is best seen by reference to FIG. 16, which is a screen shot from one embodiment of the present invention. Referring now to FIG. 16, screen shot 364 includes viewer tab 250, visual controls tab 252, subwindow area 254, and cross hair button 272, all of which correspond to their counterparts of FIG. 13. Subwindow area 254 includes subwindows 344, 346, 348 and 350, which like the subwindows of FIG. 13, display a three-dimensional view (in subwindow 344) and three two-dimensional views (in subwindows 346, 348 and 350). Subwindow 346 has cross hairs 352 and 354 subwindow 348 has cross hairs 356 and 358; and, subwindow 350 has cross hairs 360 and 362. Not apparent from FIG. 16 is that each of the lines of the cross hairs is colored to show the plane to which each corresponds. Cross hair 352 and cross hair 362 are the same color as the border of the image shown in subwindow 348; cross hair 354 and cross hair 358 are the same color as the border of the image shown in subwindow 350; and, cross hair 356 and cross hair 360 are the same color as the border of the image shown in subwindow 346.

Still referring to FIG. 16, to change between slices in a particular two-dimensional view subwindow, such as subwindow 346, 348 or 350, the user selects cross hair button 272. To change one MPR view to display a different slice, the user presses the right mouse button and drags the cross hair line in either of the other two views that is the same color as the border of the view the user wishes to change. To change two MPR views to display different slices by dragging, the user presses the right mouse button to drag the intersection of the cross hair lines that are of the same colors as the colors of the borders of the two MPR views the user wishes to change. To change two MPR views to display different slices by clicking, the user positions the cursor at the desired intersection of the intersection of the cross hair lines, and clicks the left mouse button. For example, as shown in FIG. 16, the user may wish to change the slice shown in subwindow 348. Subwindow 348 has a border having the same color as cross hair 352 of subwindow 346. Therefore, the user moves cross hair 352 to change the slice shown in subwindow 348. To get out of cross hair mode, the user selects arrow button 268.

Referring back to FIG. 13, this embodiment also permits a user to move smoothly through a series of slices. In the case where nine MPR views are displayed in subwindow area 254 (for example, as when nine-subwindows button 256 of FIG. 13 is selected), the user clicks and drags the left mouse button to accomplish this movement. In the case where less than nine MPR views are displayed in subwindow area 254 (for example, as is the case in FIG. 13), the user positions the user within an MPR view and presses and holds the right mouse button. Furthermore, one embodiment permits a user to magnify or reduce any MPR view, while the user is in cross hair mode (i.e., cross hair button 272 is selected). To increase magnification, the user holds down the right and the left mouse buttons and drags the cursor up towards the top of the screen. To decrease magnification, the user again holds down the right and the left mouse buttons, but instead drags the cursor down towards the button of the screen.

Finally, one embodiment permits stereo viewing of images. Stereo viewing creates a realistic three-dimensional effect, with the right and the left eye of the user literally seeing different images to create the illusion of depth. Stereo viewing requires in one embodiment that a stereo viewing emitter and a pair of stereo viewing glasses coupled to the workstation on which the invention is implemented. An example of such a stereo viewing emitter and glasses is the CrystalEyes equipment available from StereoGraphics, Inc. Referring to FIG. 14, selecting one-subwindow button 260, and then clicking the stereo viewing check box (not shown), causes the image displayed in subwindow 320 of FIG. 14 to fill the entire screen, and appear to be in three dimensions.

CONTRAST SHADING, TRIM, TRANSPARENCY AND COLOR CONTROLS

Contrast shading gives an image visual contrast. With no shading, a rendered image of a thick or dense object is displayed as a uniformly bright, white mass (in the case where no color has been set). Adjusting the shading permits variations to be seen more distinctly. The contrast shading feature permits adding shading to either the whole volume of the rendered image, or only to voxels having a particular range of voxel values. One embodiment of the invention provides a number of different predefined shading settings that are useful in specific anatomical structures. Shading is best used when there is no or little color, because color differences themselves provide sufficient visual distinction, which shading then may blur.

Referring back to FIG. 13, selecting an alternative presented within contrast options menu 280 sets presets for window slider 282, level slider 284, and shading slider 286. Window refers to the range of voxel values to which contrast is applied, while level refers to the center of that range. For example, with respect to eight bit voxel data, the full range would be 256, with a level of 128. However, a user may wish to apply contrast for only a limited range of voxel values. Setting the range as 60, with a level of 110, means that voxel values in the range of 80 to 140 are affected, since the range is 60 (140 minus 80), with a center of 110 (the level).

Shading slider 286 permits control of the luminescence (contrast) of the region selected in menu 280, or through sliders 282 and 284. Shading slider 286 has a range of 0.0 to 4.0. Default shading is 1.0. A setting of 1.0 creates an effect similar to lighting, such that black is added to the image—the lowest value becoming pure black, the next to the lowest becoming less black, and so forth linearly, up to the highest value, which has no black. That is, a setting of 1.0 changes the luminescence (contrast) of the voxel values selected by window slider 282 and level slider 284 in a linear fashion, from least luminescence (maximum contrast) at the lowest end of the range, to maximum luminescence (least contrast) at the highest end of the range.

Furthermore, a setting of less than 1.0 changes the luminescence (contrast) of the voxel values selected by windows slider 282 and level slider 284 in a non-linear fashion, such that maximum luminescence is reached more quickly. A setting of 0.0, therefore, means that each of the voxel values within the range has maximum contrast (minimum luminescence). A setting of greater than 1.0 changes the contrast of the range of voxel values in a non-linear fashion as well, but such that maximum luminescence is reached less quickly than if the setting were 1.0. In other words, setting shading slider 286 to 0.0 corresponds to the situation where no black is added. The image becomes bright. As shading slider 286 is moved from 0.0 to 4.0, contrast increases in the image more quickly (i.e., luminescence is increased less quickly).

When shading is applied to only a particular range of voxel values, voxel values outside the specified range lose their visual distinction. All of the values below the first value of the window have zero luminescence (maximum contrast); they all appear black. All of the values above the last value of the window have the maximum luminescence (least contrast); that is, they appear white if no color is being applied.

Contrast interacts with other features, as described hereafter, such as lighting, transparency and color. Lighting affects any contrast that has been added to an image. Transparency settings interact with contrast; increasing contrast typically darkens many regions of a partly transparent image, and therefore may require shading to be decreased. Finally, when contrast is low, colors appear with bright, pure hues, and as contrast is increased, colors at the low end of the range become increasingly dark.

Trim permits a user to create a subvolume, thereby increasing rendering speed by working with a smaller set of data. A subvolume can be created by removing extraneous data from any or all three of the orthogonal (axial, superior, and coronal) axes of a volume. Upon selection of trim mode, the cursor changes shape to a square. Clicking the left mouse button and dragging creates a rectangular trim outline bordering the area to be removed from view. Releasing the mouse button completes the process, at which time all MPR and volume views are rerendered with the outlined data trimmed from them. Selection of full volume button 274 permits redisplay of the full volume.

Transparency permits a user to see through one part of a three-dimensional image so that other parts behind the first part are visible. Rendering unimportant features transparent and rendering important features more opaque provides for the best possible analysis of the image data. Without transparency, only the outside surface of an image is visible, and the internal features are completely hidden. Note that transparency does not affect the integrity of the original data values.

Figure 17A:
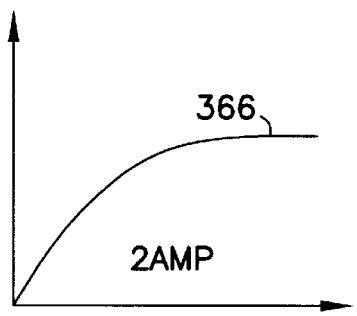
FIG. 17(a) is a graph illustrating the ramp transparency function, as can be selected from the examination viewer component.
Figure 17B:
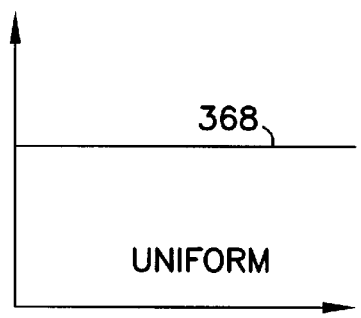
FIG. 17(b) is a graph illustrating the uniform transparency function, as also can be selected from the examination viewer component.
Figure 17C:
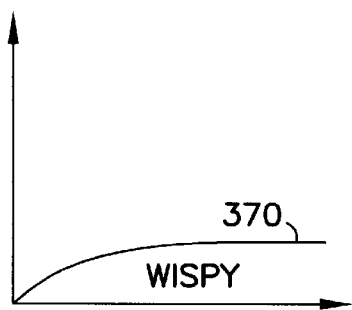
FIG. 17(c) is a graph illustrating the wispy transparency function, as also can be selected from the examination viewer component.

Seven transparency functions are shown in FIG. 17(a)–17(f). Referring now to FIG. 17(a), the ramp transparency function is shown. Function 366 maps opaqueness on the y axis to voxel values on the x axis. As shown in FIG. 17(a), the higher the voxel value for a particular voxel, the more opaque that voxel is. Referring next to FIG. 17(b), the uniform transparency function is shown. Function 368 also maps opaqueness on the y axis to voxel values on the x axis. As shown in FIG. 17(b), the opaqueness of a voxel does not change in accordance with its voxel value. Referring next to FIG. 17(c), the wispy transparency function is shown. Function 370 also maps opaqueness on the y axis to voxel values on the x axis. As shown in FIG. 17(c), opaqueness increases with voxel value, but there is a lesser range between the most opaque and the most transparent voxel values over the range of voxel values, as compared with function 366 of FIG. 17(a).

Figure 17D:
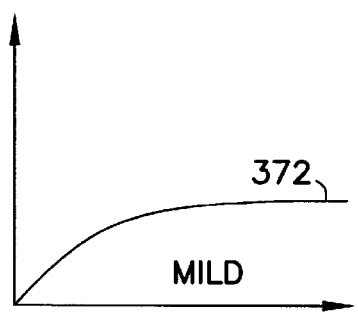
FIG. 17(d) is a graph illustrating the mild transparency function, as also can be selected from the examination viewer component.
Figure 17E:
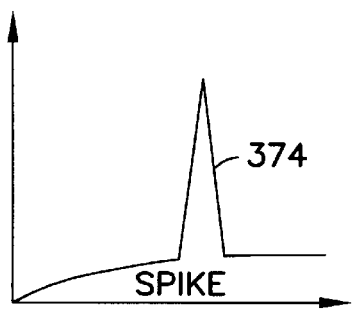
FIG. 17(e) is a graph illustrating the spike transparency function, as also can be selected from the examination viewer component.
Figure 17F:
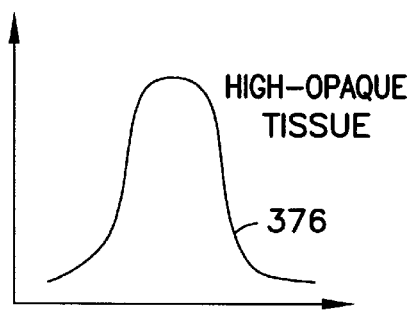
FIG. 17(f) is a graph illustrating the high-opaque transparency function, as also can be selected from the examination viewer component.
Figure 17G:
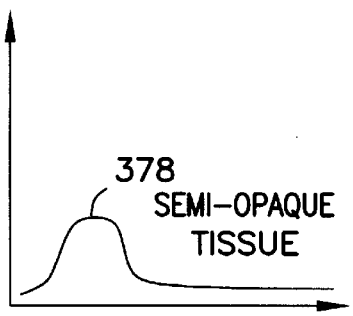
FIG. 17(g) is a graph illustrating the semi-opaque transparency function, as also can be selected from the examination viewer component.

Referring next to FIG. 17(d), the mild transparency function is shown. Function 372 maps opaqueness on the y axis to voxel values on the x axis. As shown in FIG. 17(d), opaqueness increase with voxel value, more steeply than with function 370 of FIG. 17(c), but not as steeply as with function 366 of FIG. 17(a). Referring next to FIG. 17(e), the spike transparency function is shown. Function 374 also maps opaqueness on the y axis to voxel values on the x axis. As shown in FIG. 17(e), opaqueness is very high for a small range of voxel values, but otherwise is very low. Referring next to FIG. 17(f), the high-opaque tissue transparency function is shown. Function 376 maps opaqueness on the y axis to voxel values on the x axis. As shown in FIG. 17(f), opaqueness is very high for a small range of voxel values, similar to function 374 of FIG. 17(e), but the drop-off to the otherwise lower opaqueness levels is not as steep. Referring next to FIG. 17(g), the semi-opaque tissue transparency function is shown. Function 378 maps opaqueness on the y axis to voxel values on the x axis. As shown in FIG. 17(g), opaqueness is high only for a small range of voxel values, similar to function 376 of FIG. 17(f), but does not reach the levels of opaqueness as does function 376.

As those of ordinary skill within the art will appreciate, no embodiment of the present invention is limited to any particular transparency functions. That is, an embodiment may have only a subset of the functions that have been described. Alternatively, an embodiment may have completely different functions. Alternatively still, an embodiment may have some of the functions that have been described, and some other functions.

Referring back to FIG. 13, a user controls the transparency of a view by selecting a transparency function from menu 288. Slider 290 controls the scaling of the function as selected from menu 288. Setting the slider to the left means that those voxel values having a high opacity value on the selected transparency function are very opaque relative to those voxel values having a low opacity value on the selected transparency function. That is, the scaling is such that the opacity of the voxel values already having high opacity values as defined by the function are further accentuated. Setting the slider to the right means that the scaling factor is such that the opacity values of all of the voxel values effectively are zero. That is, the scaling is such that the transparency function curve is "pushed down" so that the voxel values having the greatest opacity still have an opacity not much more than the voxel values having the least opacity.

With respect to color, one embodiment uses a variety of color schemes, including gray scale, for displaying images. It accomplishes this by assigning a particular (unique) color to all of the voxels having a specific value. Since different types of tissue tend to have different voxel values (for example, for CT data, soft tissue tends to have lower voxel values and more dense objects tend to have higher voxel values), this means that different types of tissue appear in different colors.

Each voxel value has a red, green, and blue value assigned to it, by virtue of a color table mapping color values to each voxel value or range of voxel values. The proportion of each of these colors determines a voxel's color. For instance, if all of the voxels of a specific value, such as 128, have a color scheme of red equals one, green equals zero, and blue equals zero, the voxels of value 128 all appear red. Conversely, if the color scheme is red equals zero, green equals one, and blue equals zero, they all appear green.

One embodiment provides a number of different preset color schemes, each suitable for viewing specific types of tissue. Each color scheme highlights or visually emphasizes tissues with specific voxel values while de-emphasizing other voxel values. Still referring to FIG. 13, the different color presets are selected via color menu 292. Color menu 292, then, is a high-level control because it provides presets for a number of specific color qualities (i.e., the red, green and blue values for voxels having a particular voxel value).

SLICE OPTIONS

When examination viewer component 114 is first entered from image gallery component 112, the MPR two-dimensional images automatically show the middle slice of the viewing orientation, as identified by the cross hairs within the subwindows, as has been discussed. These slices, or any slice chosen by the cross hairs within the subwindows, may be enhanced through slice options. One embodiment permits slices to be made transparent, to acquire color, to be made oblique, and/or to have thickness.

Still referring to FIG. 13, as has been discussed, transparency menu 288 and transparency slider 290 permit control of the transparency of the images shown in the subwindows. These controls always apply to the three-dimensional image, such as the three-dimensional image shown in subwindow 314. However, for the settings controlled by menu 288 and slider 290 to apply to two-dimensional MPR images, such as those in subwindows 310, 312 and 314, transparent check box 294 must be selected.

Similarly, as has been discussed, color menu 292 permits control of the color of the images shown in the subwindows. The color preset specified via color menu 292 always applies to the three-dimensional image, such as that shown in subwindow 314. However, for the preset specified within color menu 292 to apply to two-dimensional MPR images, such as those in subwindows 310, 312 and 314, color check box 296 must be selected.

Figure 18:
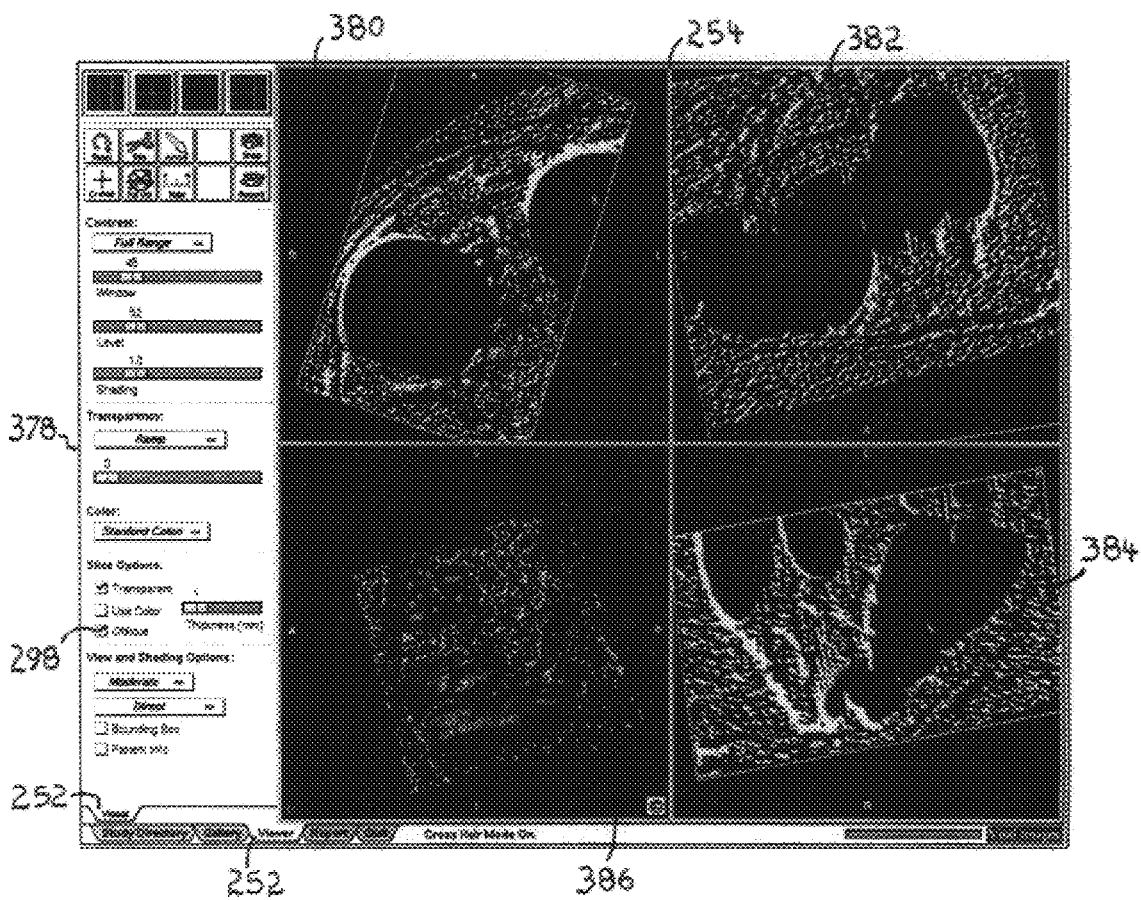
FIG. 18 is another screen shot from an embodiment of the present invention, also showing the examination viewer component, and in particular showing the MPR views when the oblique check box is selected.

As has been explained, subwindows 310, 312 and 316 typically display the three orthogonal views of the three-dimensional volume displayed in subwindow 314. That is, each of subwindows 310, 312 and 316 cuts a slice of the volume displayed in subwindow 314 across one of the three standard axes, axial, coronal, and superior. However, selection of oblique check box 298 renders the three two-dimensional views of subwindows 310, 312 and 316 in an oblique orientation, as opposed to an orthogonal orientation. This is specifically shown in FIG. 18. Referring now to FIG. 18, screen shot 378 includes viewer tab 250, visual controls tab 252, subwindows area 254, and oblique check box 298, all of which correspond to their counterparts of FIG. 13. Oblique check box 298 is selected in FIG. 18. As a result, subwindows 380, 382 and 384, which correspond to subwindows 310, 312 and 316 of FIG. 13, display two-dimensional MPR views that are oblique. Rotation of the volume with oblique check box 298 selected correspondingly changes the viewing orientation within subwindows 380, 382 and 384.

Referring back to FIG. 13, thickness slider 300 permits a user to enlarge the size of the slices shown in the MPR views of subwindows 310, 312 and 316. That is, slider 300 permits a thicker rendering of the slices of the MPR views—the MPR views are transposed from being two-dimensional to being three-dimensional. Thicker slices are in actuality mini-volumes or slabs. Thickness is useful in unison with transparency, to permit a user to see through unimportant features of a slice to structures of interest farther in. Thickness cannot be increased past the default value if transparency is not being used.

VIEWING AND LIGHTING (SHADING) OPTIONS

Still referring to FIG. 13, orthographic and perspective viewing menu 302 permits choosing among the orthographic viewing mode and the various perspective viewing modes. In the perspective viewing mode, parallel lines of an object converge, making distant parts of the image appear smaller. Conversely, the orthographic mode makes all lines of an object perpendicular to the plane of projection. Two-dimensional MPR images are always displayed in orthographic mode, while either orthographic or a perspective mode can be selected for three-dimensional images.

Within one embodiment of the invention, several different options are selectable via menu 302: orthographic, telephoto, moderate, and wide angle. All options except orthographic refer to perspective modes. The specific options available depend on the protocol selected within the image gallery component. When in a perspective mode, a field of view cone is displayed on each image to indicate how wide the field of view is. The telephoto perspective mode eliminates peripheral image data from the view; the moderate perspective mode views an image with a wider field of view than the telephone mode; and, the wide angle perspective mode views the image with the widest provided field of view. As those skilled in the art will appreciate, however, no embodiment of the present invention is particularly limited to any particular set of orthographic and perspective mode options.

The actual options selectable within menu 302—that is, the actual options available within menu 302—are set as part of a particular protocol selected for a given set of voxel data. In addition, as to a particular option, the actual settings of that option are also selected by the protocol. For example, one protocol may set a wider field of view for the wide angle perspective mode than does another protocol.

Lighting refers to a light source that shines on a volume, to illuminate the volume and allow the user to see the volume more clearly. No embodiment of the invention is limited to any particular lighting options. However, within one embodiment, the normal, minimum-intensity-projection (MINIP) and maximum-intensity-projection (MIP) options are always available. The normal option turns lighting off, while the MIP option displays only the highest voxel values of an image along each viewing ray. The MIP option is useful when the feature of interest within an image is composed of the highest voxel values and competing features are obscuring it. Lighting is selected via lighting menu 304.

ANNOTATIONS

Figure 19:
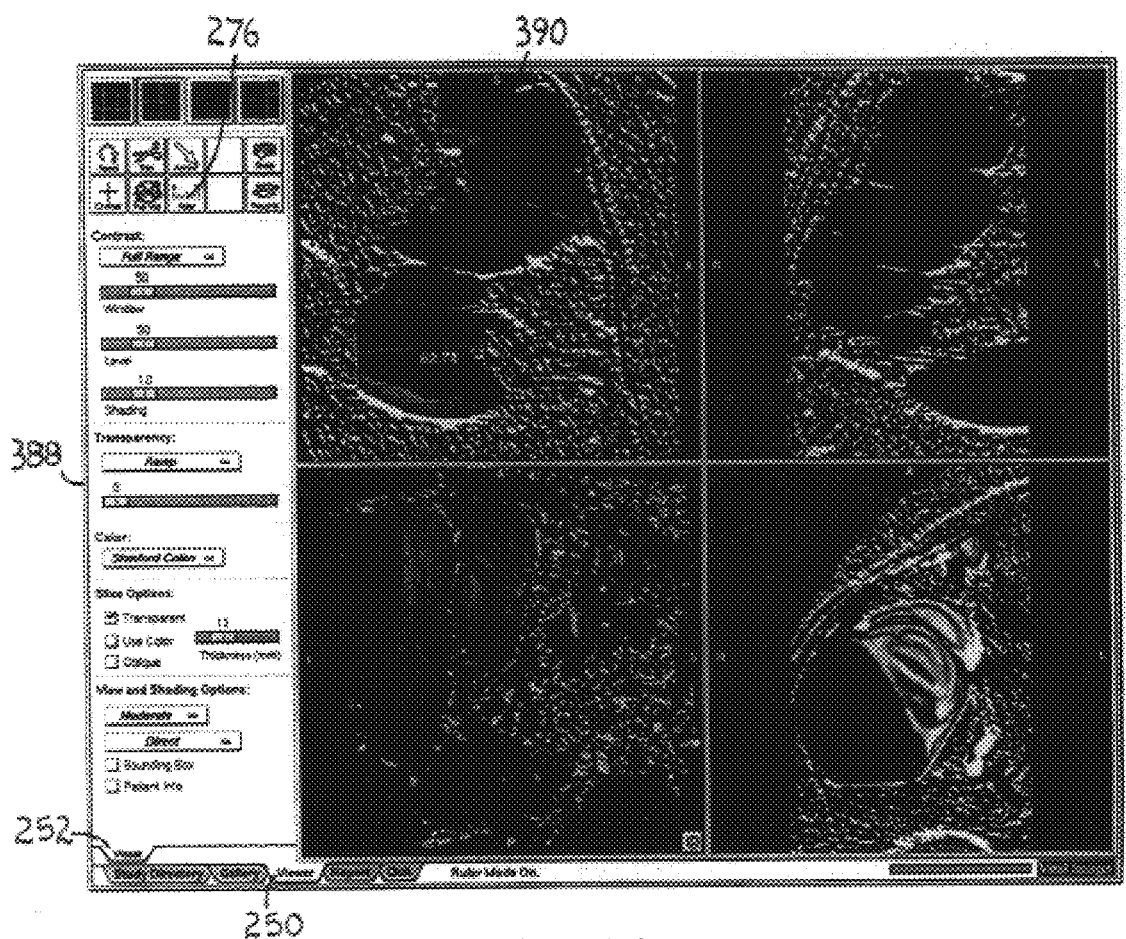
FIG. 19 is another screen shot from an embodiment of the present invention, also showing the examination viewer component, and in particular showing the addition of a ruler to a view of an image.

One embodiment of the invention permits a user to add rulers to an image to indicate the size of features therein. This is shown in FIG. 19, which is a further screen shot of one embodiment of the invention. Referring now to FIG. 19, screen shot 388 includes viewer tab 250, visual controls tab 252 and ruler button 276, all of which correspond to their counterparts of FIG. 13. Placement of a ruler is accomplished by selection of ruler button 276, positioning the cursor at the desired beginning location of the ruler, clicking on the mouse button, dragging the mouse to the desired end location of the ruler, and then releasing the mouse button. This embodiment then places a ruler in the desired position, with a labeled measurement indicating the shown distance in millimeters. For example, ruler 390 shows that the distance of the shown image is 82.74 millimeters.

Figure 20:
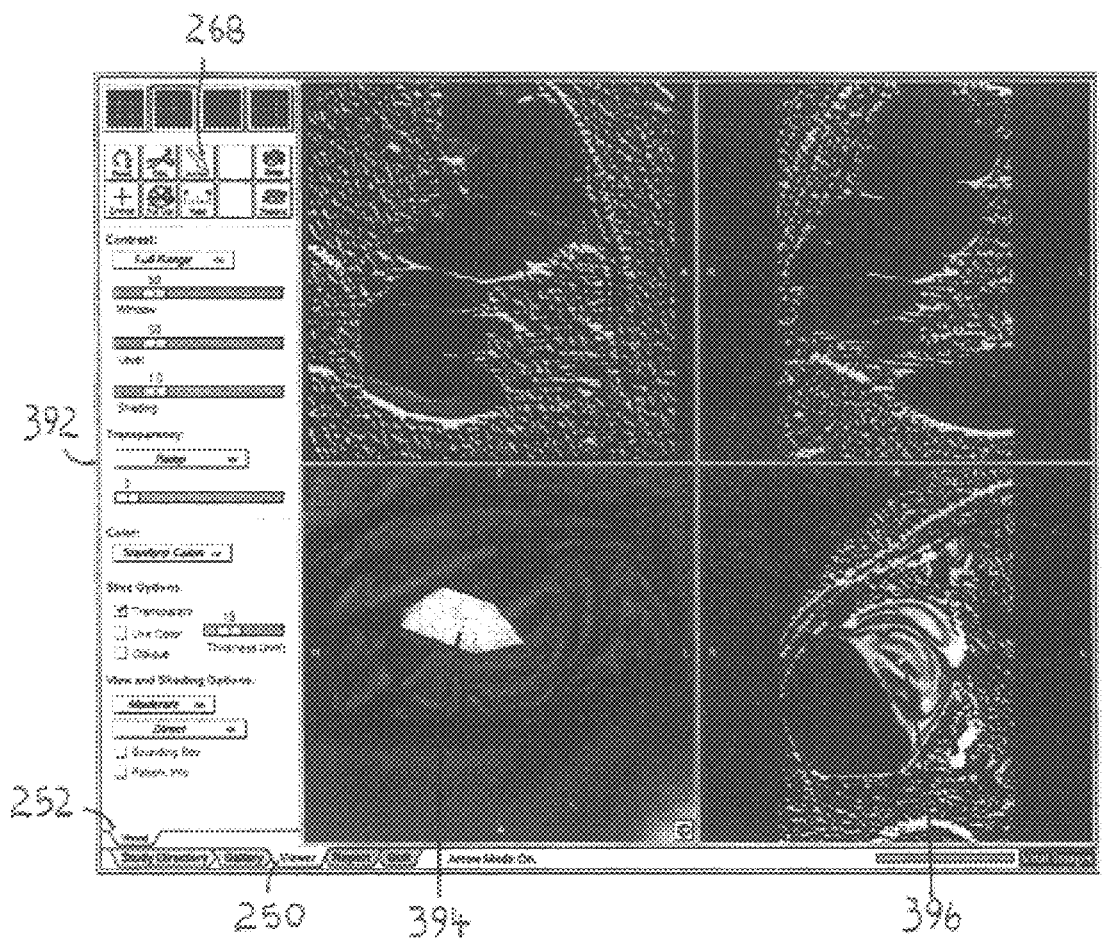
FIG. 20 is another screen shot from an embodiment of the present invention, also showing the examination viewer component, and in particular showing the addition of an arrow to a view of an image.

One embodiment also permits a user to place an arrow within an image to point out a specific feature therein. This is shown in FIG. 20, which is another screen shot of one embodiment of the present invention. Referring now to FIG. 20, screen shot 392 includes viewer tab 250, visual controls tab 252, and arrow button 268, all of which correspond to their counterparts of FIG. 13. Placement of an arrow is accomplished by selection of arrow button 268, positioning of the mouse to a desired beginning location within an image, clicking the mouse button, dragging the mouse to a desired end location within the image, and releasing the mouse button. This embodiment then places an arrow within the image, rerendering all other images to show the arrow. For example, as shown in FIG. 20, arrow 394 within one image corresponds to arrow 396 in another image. The arrow is embedded within the image, in that it is displayed in three dimensions, and can be viewed from different angles as the perspective for the image changes. That is, the arrow is a geometrical model (i.e., a cylinder having a capping cone). Note that the arrow does not actually become a part of the image data; it does not replace any voxel data previously acquired. Rather, the arrow is embedded within the image as displayed.

Figure 21:
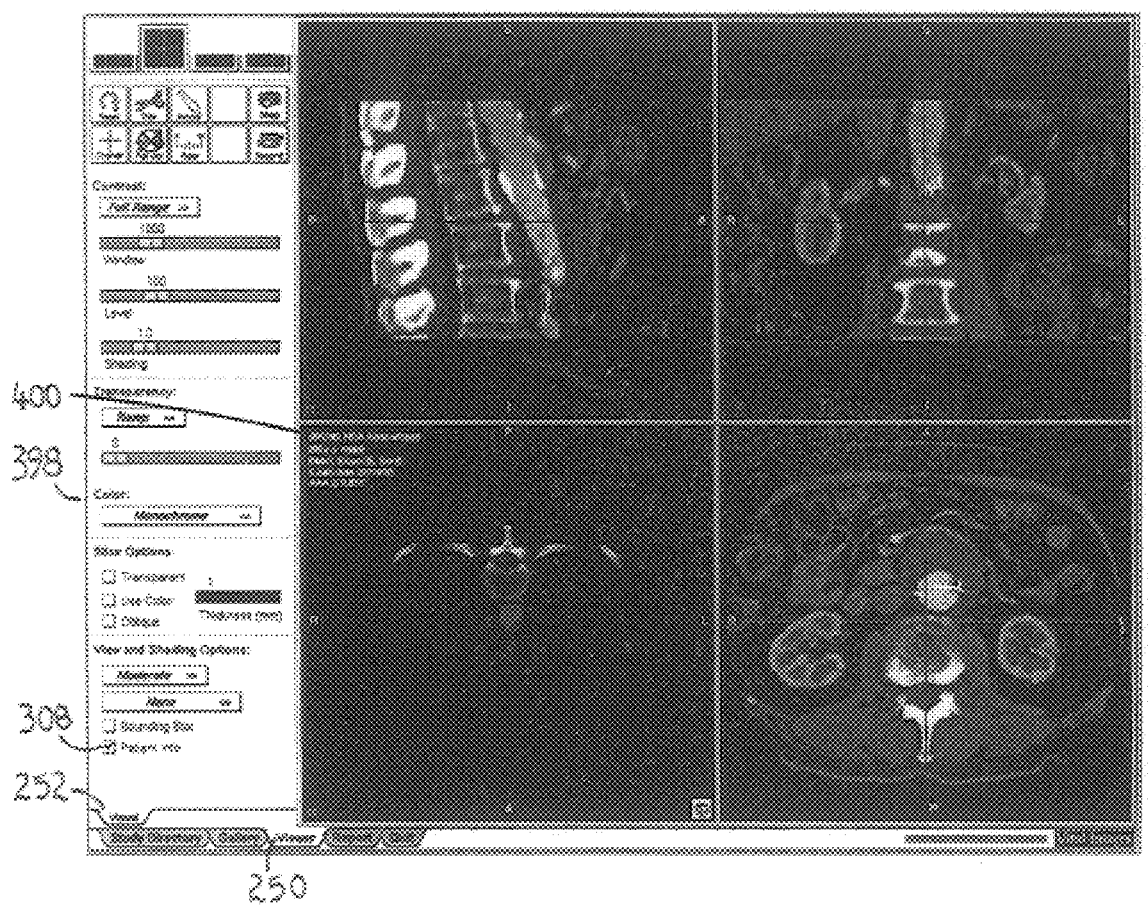
FIG. 21 is another screen shot from an embodiment of the present invention, also showing the examination viewer component, and in particular showing the addition of information regarding a particular patient study to a view of an image.

As has been discussed, the image data retrieved by the retrieve data set component includes information regarding a particular patient study as well as the image data itself. One embodiment permits a user to add this information to the images, as is shown in FIG. 21, which is a snap shot from one embodiment of the invention. Referring now to FIG. 21, screen shot 398 includes viewer tab 250, visual controls tab 252, and patient information check box 308, all of which correspond to their counterparts of FIG. 13. Placement of patient information is accomplished by selection of patient information check box 308. The patient information is placed within the three-dimensional image of the data, such as patient information 400 of FIG. 21.

OUTPUT OF THE EXAMINATION VIEWER COMPONENT

As has been discussed, the output to the examination viewer component includes snapshots taken of particular views of the images under examination in the component, as well as video output of the views. Referring back to FIG. 13, upon manipulation of the visual controls within visual controls tab 252 to obtain a desired view, a user selects snapshot button 270, moves the cursor over a desired view of the image, and clicks the mouse button to save the view as an output of the examination viewer component. The user is not limited to any particular number of images. Snapshots can be taken at any time during examination of the views of an image, and each snapshot is saved for further review in the report generator/viewer component, as is described hereafter.

Furthermore, one embodiment of the invention permits a user to record a video or "movie" of the views of the image shown on the display device of the workstation. This is accomplished by coupling a video cassette recorder or other appropriate device to an output port of the workstation. Still referring to FIG. 13, the user selects record button 278, which causes this embodiment to also send the display output shown on the display device concurrently to the output port to which the video cassette recorder is coupled. Depression of the record button on the video cassette recorder then begins recording the display output on a video cassette inserted into the video cassette recorder. This embodiment permits the user to modify the views of the image shown via manipulation of the visual controls of visual controls tab 252 as has been heretofore described. Depression of the stop button on the video cassette recorder, followed by deselecting recorder button 278, stops the recording process.

As has been described in conjunction with FIGS. 13–21, the examination viewer component (i.e., component 114 as shown in FIG. 2 and FIG. 12) permits a user to modify various views of an image selected from the image gallery component (i.e., component 112 of FIG. 2 and FIG. 9). The screen shots of FIGS. 13–21 are from one embodiment of the present invention. The controls within visual controls tab 252 permit a user to manipulate one or more views of the selected image, as the views are shown within subwindows area 254. The controls within visual controls tab 252 are preset in accordance with the selected protocol for the image, to provide the user with a good starting point from which to view the data. However, one embodiment permits a user to adjust the controls individually, so as to best examine views of the image. In various pop-up menus, such as menus 280, 288, 292, 302, and 304, one embodiment provides an intermediate level of control between direct manipulation of the slider controls and the presets dictated by the protocols. When the user has manipulated the controls desired, and has determined that a particular view of the image should be saved for later analysis, One embodiment permits the user to either save a snapshot of the image via selection of snapshot button 270, or record a video of the image as it is shown on the display device via selection of record button 278.

REPORT GENERATOR/VIEWER COMPONENT

Figure 22:
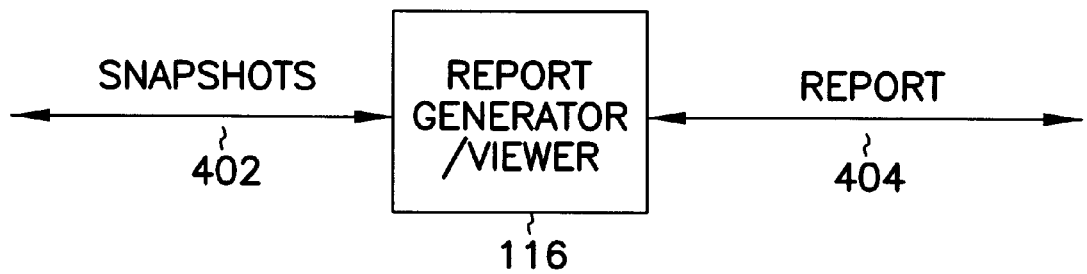
FIG. 22 is a block diagram showing in more particular the report generator/viewer component of FIG. 2.

Referring now to FIG. 22, report generator/viewer component 116 is shown in more particular. Input 402 to reporter generator/viewer component 116 includes one or more snapshots as chosen by the user within examination viewer component 114. The snapshots are particular views of the image selected within image gallery component 112, as modified and selected within examination viewer component 114. Output 404 to reporter generator/viewer component 116 is a report including selected snap shots from the snapshots of input 402, along with other information such as patient information, as desired by the user, as well as formatting information regarding how the selected snapshots are to be organized. The report of output 404 typically includes a header giving the title of the report. Report generator/viewer component 116 supports two different output modes: a traditional filming format in which the user, such as a radiologist, is able to rearrange the snapshot layout before printing to film, and a multimedia report format in which the user is also able to type comments in a separate textual field, and type text on the snapshot images themselves.

Figure 23:
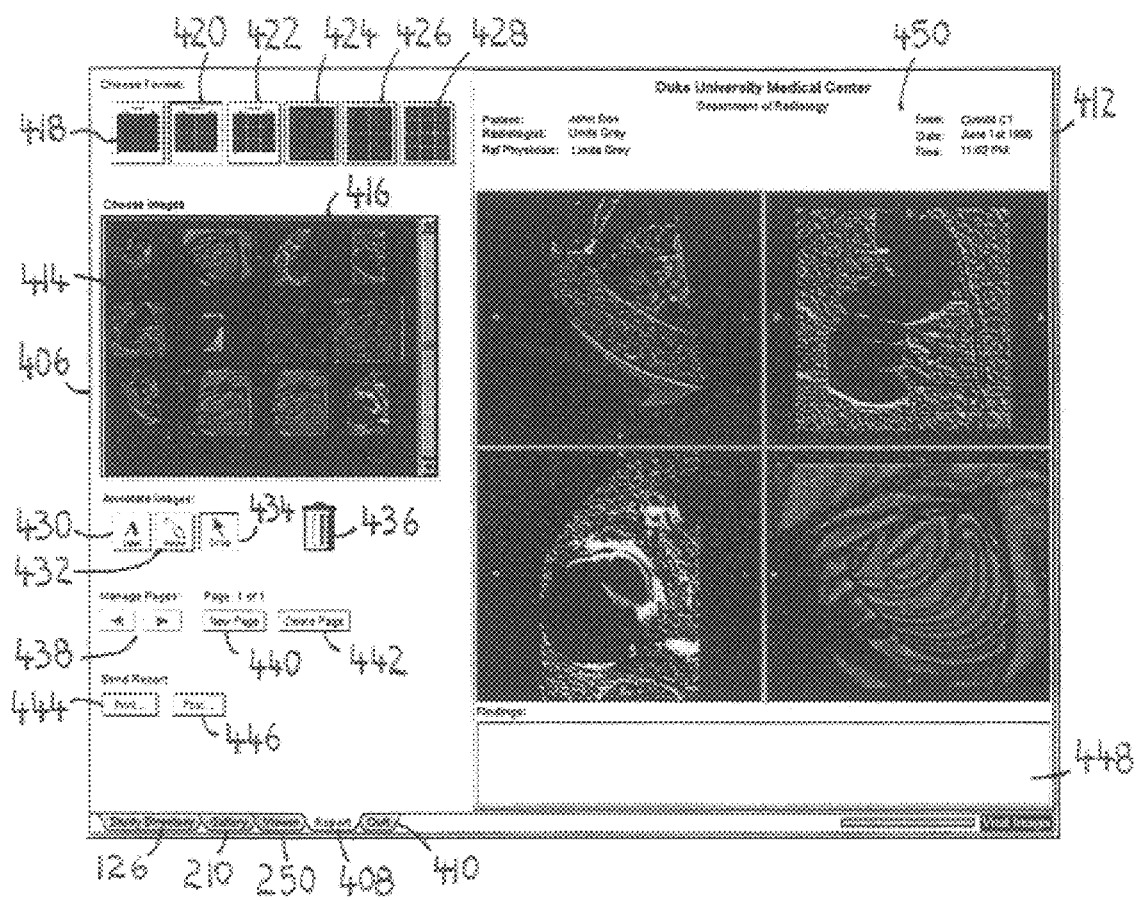
FIG. 23 is a screen shot from an embodiment of the present invention, showing the report generator/viewer component.

Report generator/viewer component 116 provides a variety of tools to permit the user to rearrange the snapshots in a desired manner, and annotate the snapshots accordingly. The component permits arrangement according to any of the formats of examination viewer component 114, as have been already described. The component provides two annotation tools, a text tool to permit the insertion of text into an image, and an arrow tool to create an arrow within an image. These features are shown by reference to FIG. 23, which is a screen shot from one embodiment of the present invention. Referring now to FIG. 23, screen shot 406 includes study directory tab 126 (identical to study directory tab 126 as shown in FIG. 4), gallery tab 210 (identical to gallery tab 210 as shown in FIG. 10), viewer tab 250 (identical to viewer tab 250 of FIG. 13), report tab 408, and quit tab 410.

One embodiment of the invention permits a user to go back to any previously described component by selection of its corresponding tab. Thus, the user may go back to retrieve data set component 108 via selection of study directory tab 126, to image gallery component 112 via selection of gallery tab 210, and to examination viewer component 114 via selection of viewer tab 250. To subsequently return to report generator/viewer component 116, the user then selects report tab 408. This back-and-forth process is most useful in the case of reversion back to the examination viewer component 114, in the situation where the user has neglected to take a snapshot of a desired view of the image, and has not realized this until the user is within report generator/viewer component 116. Finally, the user may quit via selection of quit tab 410.

Still referring to FIG. 23, screen shot 206 also comprises report area 412, choose images area 414, scroll bar 416, format buttons 418, 420, 422, 424, 426, and 428, label button 430, arrow button 432, drag button 434, trash icon 436, manage page buttons 438, new page button 440, delete page button 442, print button 444, and post button 446. Report area 412 includes findings area 448 and patient information area 450 in accordance with the format selected. The format buttons specifically include one-image-with-findings button 418, four-images-with-findings button 420, nine-images-with-findings button 422, one-image-no-findings button 424, four-images-no-findings button 426, and twelve-images-no-findings button 428.

The number of images displayed in report area 412, and whether report area 412 includes findings area 448 and patient information area 450 as is shown in FIG. 23, is determined by the selection of a report format via buttons 418, 420, 422, 424, 426 and 428. Selecting button 418 displays one image within report area 412, as well as findings within findings area 448 and patient information within patient information area 450. Selecting button 420 displays four images within report area 412, as well as findings within findings area 448 and patient information within patient information area 450. Report area 412 as shown in FIG. 23 is in accordance with the selection of button 420. Selecting button 422 displays nine images within report area 412, as well as findings within findings area 448 and patient information within patient information 450.

Figure 24:
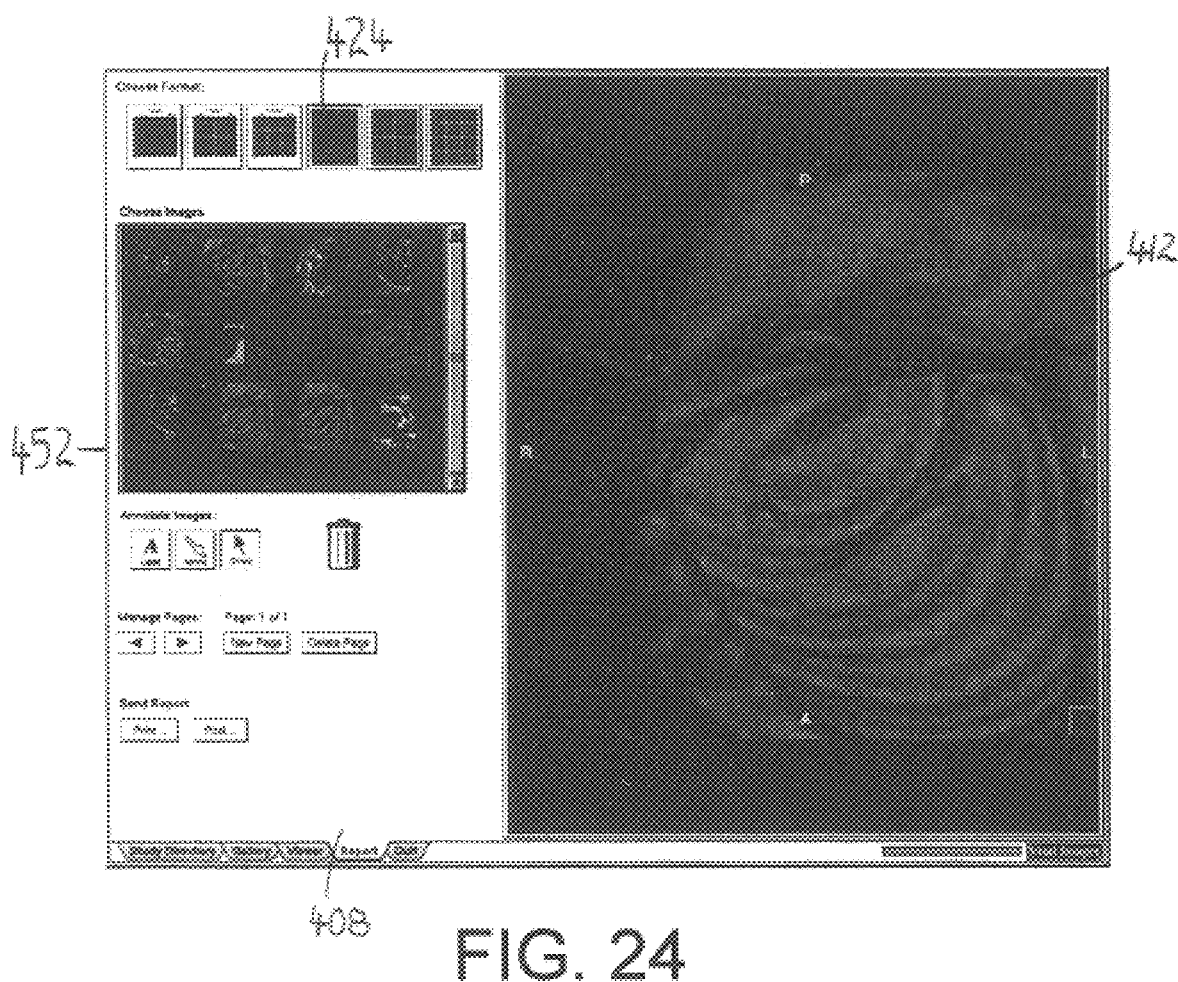
FIG. 24 is another screen shot from an embodiment of the present invention, also showing the report generator/viewer component; and, FIG. 25 is a block diagram showing in more particular the print and post component of FIG. 2.

Still referring to FIG. 23, selecting button 424 displays one image within report area 412, such that the image takes up the entirety of report area 412, without the display of either findings area 448 or patient information area 450. This is shown in FIG. 24, which is another snap shot from one embodiment of the invention. Referring now to FIG. 24, snap shot 452 includes report tab 408, report area 412, and button 424, all of which correspond to their counterparts of FIG. 23. Report area 412 of FIG. 24, however, displays one image without the display of patient information or findings information, as is the case with report area 412 of FIG. 23, which displays patient information within patient information area 412 and findings information within findings information area 448. Referring back to FIG. 23, selecting button 426 displays four images within report area 412, such that the image takes up the entirety of report area 412, without display of either findings area 448 or patient information area 450. Similarly, selecting button 428 displays twelve images within report area 412, such that the image takes up the entirety of report area 412, without display of either findings area 448 or patient information area 450.

Placement of images within report area 412, regardless of the report format selected, is accomplished in drag and drop mode, which is entered by selection of drag button 334. Thumbnails of the snap shots of the views of the image taken in the examination viewer component are shown in choose images area 414. If there are more snap shots than can be displayed at one time within area 414, scroll bar 416 permits scrolling to view the undisplayed snap shots. To place an image within report area 412, the user positions the mouse over the desired view within area 414, presses and holds down the left mouse button, and drags the view to the desired location within area 412. Release of the mouse button then "drops" this view at the desired location, and the view appears, appropriately sized. This process is repeated until the desired views are displayed within report area 412. Furthermore, any view within report area can be "dropped over" with a new view selected from area 414. To remove an image from report area 412, the image is selected, and dragged and dropped over trash icon 436. Similarly, to remove an image from choose images area 414, the image is selected, and dragged and dropped over trash icon 436.

Report area 412 shows the current page of the report. One embodiment permits the creation of more than one page, however. To create an additional page, new page button 440 is selected, which clears report area 412. To navigate among the pages of a report, either manage button 438 is selected. If after creation of a new page the user desires to delete the page, the user may press delete page button 442. No embodiment of the present invention is limited to any particular number of pages within a report; any report within an embodiment of the invention may have any number of pages.

One embodiment permits a user to add arrows to a report to particularly point out features of interest on the images shown. Placement of an arrow is accomplished in arrow mode, which is entered by selection of arrow button 432. To place an arrow within an image displayed in area 412, the user positions the cursor to the desired beginning location of the arrow, presses and holds down the left mouse button, drags the mouse to the desired ending location of the arrow, and finally releases the mouse button. The size of the arrow is limited by the format chosen for area 412. That is, an arrow cannot extend over two images within report area 412. Repositioning of an arrow is accomplished within drag and drop mode, selected via button 434. An arrow may also be deleted by dragging it over trash icon 436.

One embodiment also permits a user to label features of interest within an image of a report. Labeling of features of interest is accomplished within label mode, which is entered by selection of label button 430. To add a label within an image displayed in area 412, the user positions the cursor to the desired location of the label, and clicks the left mouse button. The user then types the desired text, and presses enter on the keyboard to finish text entry. Repositioning of labeled text is also accomplished within drag and drop mode, selected via button 434, and text may be deleted by dragging it over trash icon 436.

In addition, one embodiment permits a user to add findings to a particular page of a report, in findings area 448, if a report format is selected that permits such findings to be added. That is, findings can be added in report formats selected by buttons 418, 420 and 422, but not by those selected by buttons 424, 426 and 428. To add findings, the user moves the cursor to the findings area 448, and clicks the mouse button. The user then types the desired text, and presses enter on the keyboard to finish the text entry. Conversely, the patient information within patient information area 412 is automatically added to the report pages via the image data, as retrieved from the retrieve data set component. The user cannot change this information from within the embodiment. The information automatically appears when the user has selected a report format via button 418, 420 or 422.

The output of the report generator/viewer component is the complete set of report pages created by the user. The user signals that the report is complete and ready for printing or posting by selection of either print button 444 or post button 446. Pressing either button establishes as the output of the report generator/viewer component the set of report pages as has been created and modified, as well as whether either print button 444 or post button 446 has been pressed. Control then passes from the report generator/viewers component.

As has been described in conjunction with FIG. 23 and FIG. 24, the report generator/viewer component (i.e., component 116 as shown in FIG. 2 and FIG. 22) permits a user to generate and modify a report containing the snap shots of images as generated within examination viewer component 114. Buttons 418, 420, 422, 424, 426 and 428 permit a user to select the desired format of a report. The user selects images from area 414 for placement on a particular page of a report, as shown in area 412, via drag and drop mode as selected by button 434. The user can create, delete, and manipulate pages via selection of buttons 438, 440 and 442. The user can add labels and arrows via selecting button 430 and 432, respectively. If a format has been selected that allows for patient information and findings information to be displayed, the patient information is shown in area 450 of area 412, and the findings information is shown in area 448 of area 450, as entered by the user. Once the user has finished creating a report, the user selects either button 444 or 446 to print or post the report.

PRINT AND POST COMPONENT

Figure 25:
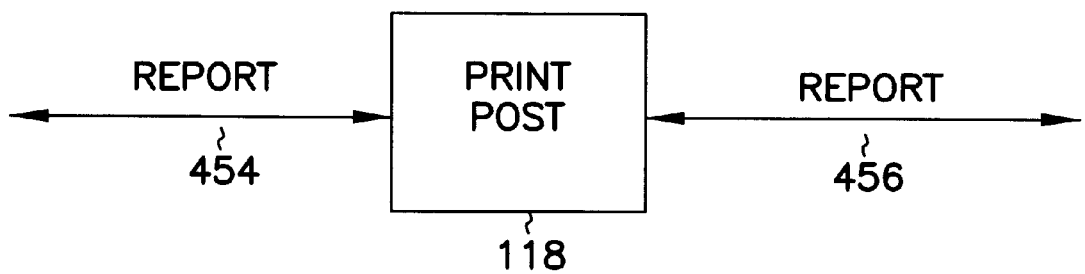

Referring now to FIG. 25, print and post component 118 is shown in more particular. Input 454 to print and post component 118 includes the report as generated within report generator/viewer component 116, as well as information as to whether either the post or the print button was pressed within report generator/viewer component 116. Output 456 to print and post component 118 includes a hard copy of the report of input 454 in the case where the print button was pressed within report generator/viewer component 116, or an electronic copy in HTML format in the case where the post button was pressed within report generator/viewer component 116.

In one embodiment of the present invention, the computer on which the invention is implemented is coupled to a DICOM-compatible printer, either point to point or over a network. The printer is either a film or a paper printer. Such printers include the Kodak 2180 laser printer, the 3M 952 laser printer, the Agfa LR 3300 laser printer, and the Codonics NP1600 color printer; however, as those of ordinary skill within the art will recognize, no embodiment of the present invention is particularly limited to any single type of printer. The output of the print and post component is a hard copy of the report generated within the report generator/viewer component.

In another embodiment of the present invention, the computer on which the invention is implemented is either coupled to an Internet or intranet web server or is also an Internet or intranet web server. In this embodiment, the output of the print and post component is one or more HTML files that may be viewed by an Internet or intranet world-wide-web browser, such as Netscape Navigator or Microsoft Internet Explorer, as is well known to those of ordinary skill within the art. The images of the output in this embodiment are converted to PNG format for correct viewing within a web browser. Posting to an Internet web server provides instant access to authorized associates of the user, such as the referring physician of the patient.

OPERATION AND ADVANTAGES OF ADV

As been hereto described in conjunction with the drawings, one embodiment of the invention permits the viewing of three-dimensional volume-rendered images of voxel data in an environment that provides the non-expert end user the ability to generate the desired volume renderings of data easily and accurately. The general work flow governed by one embodiment of the invention ensures that such a user is typically not overwhelmed. For example, within the retrieve data set component, the user is provided with only those controls that are necessary to allow the user to select and retrieve a data set component. Within the image gallery component, the user is provided a number of different images from which to select. Within the examination viewer component, the user is enabled to change the visual controls governing the viewing of a particular image. Furthermore, within the report generator and viewer component, the user is provided with only those controls necessary to generate and view a report of selected images.

Besides this segmenting of particular controls within a particular component, one embodiment of the invention also furthers work flow by enabling the user to jump among components. For example, although the logical order of work flow dictates that data is first retrieved before a gallery of images is selected, a user may after viewing the gallery of images for a particular set of data go back to the retrieve data set component and reselect a set of voxel data. Thus, if the user ever makes a mistake in selecting the wrong data set or the wrong image within one component, and does not realize this until advancing to the next component, the user always has the ability to go back to a previous component.

The protocol selector component provides the invention with powerful advantages. A set of voxel data itself is acquired through scanning from a scanning device as dictated by acquisition parameters within a protocol. This is important to ensure that the best possible voxel data is obtained. Furthermore, the protocol selection component matches the correct protocol with the set of voxel data selected, so that the initial viewing parameters regarding the set of voxel data permit a user to initially view good images of the data. That is, the initial viewing parameters (the presets of the visual controls) provided by the selected protocol allow a user to "hit the ground running" when examining a particular set of voxel data.

The protocol selector component also determines which visual controls are present within the examination viewer component. For a particular type of voxel data, different visual controls may have proven to be unnecessary or not useful in the viewing of an image of the voxel data. Rather than permit the user to nevertheless control these aspects of the visualization, the protocol may instead determine that they are not to be shown, and thus that the user may not use the controls. In this way, the protocol selector component controls the behaviors of the user as the user steps through the execution of the invention. As those skilled in the art will appreciate, the actual behaviors controlled by the protocol selector component are not limited to the visual controls as is described herein. Any behavior may be controlled as per a particular component, and lie within the scope of the claimed invention.

While the examination viewer component subsequently allows a user to change the visual controls presets as to a particular image selected within the image gallery component, the examination viewer component does this in an intelligent manner. Controls are provided to the user on two levels. For the experienced user, low-level controls are provided that enable the user to minutely change the visual characteristics as governed by the controls. For the less experienced user, high-level controls are provided that enable the user to select among certain presets of one or more of the low-level controls, since the user may be uncomfortable directly adjusting the low-level controls. The high-level controls thus provide users with an added level of control of adjustment of an image over that provided by the protocols feature, without having to succumb to individually altering the minutiae of the low-level controls.

Those of ordinary skill within the art will readily appreciate that many changes and modifications to the above drawings and description can be made without departure from the spirit or scope of the following claims. For example, one embodiment of the invention has been substantially described and shown in conjunction with data sets that are medical in nature, to assist physicians such as radiologists in making medical diagnoses. However, no embodiment of the invention is so particularly limited. Other embodiments may be applied to data sets in other domains, such as oil exploration, etc., without departing from the spirit or scope of the following claims.

I claim:

1. A computerized system for displaying a set of voxel data on a display device of a computer, the computerized system comprising:

a retrieve data component operative to retrieve the set of voxel data from a storage device operatively coupled to the computer;

a protocol selector component operative to automatically select an appropriate protocol from a set of predefined protocols, said protocol being determined by at least one field in the set of voxel data, each of said predefined protocols defining a set of viewing characteristics to be applied to the set of voxel data;

an image gallery component operative to display a gallery of volume-rendered images of the set of voxel data and providing an interface allowing the selection of one of the volume rendered images, each of said volume-rendered images displayed on the display device in accordance with the selected appropriate protocol; and an examination viewer component operative to modify the volume-rendered image selected from the gallery by adjustment of one or more visual controls governing the display of the image on the display device.

2. The computerized system of claim 1, wherein the set of viewing characteristics includes one or more attributes selected from the group consisting of: contrast, transparency, and color.

3. The computerized system of claim 1, wherein the volume-rendered images displayed in the gallery are automatically determined based on the selected appropriate protocol.

4. The computerized system of claim 1, wherein the one or more visual controls are automatically determined by the selected appropriate protocol.

5. The computerized system of claim 1, wherein the one or more visual controls are preset to a value determined by the selected appropriate protocol.

6. The computerized system of claim 1, wherein the examination viewer component further provides for the selection by a user of an alternative protocol to control the display of the volume-rendered images.

7. The computerized system of claim 1, further comprising a report component operative to generate a report based on one or more snap shots taken within the examination viewer component.

8. The computerized system of claim 1, further comprising a print and post component, to generate a copy of the report generated by the report generator.

9. A method for displaying a set of voxel data on a display device of a computer, the method comprising:

retrieving the set of voxel data;

selecting an appropriate protocol from a set of predefined protocols, said protocol being determined by at least one field in the set of voxel data, each of said predefined protocols defining a set of viewing characteristics to be applied to the set of voxel data;

displaying a gallery of volume-rendered images of the set of voxel data, each of said volume-rendered images displayed on the display device in accordance with the selected appropriate protocol; and displaying one or more visual controls operative to modify a volume-rendered image selected from the gallery.

10. The method of claim 9, wherein the set of viewing characteristics includes one or more attributes selected from the group consisting of: contrast, transparency, and color.

11. The method of claim 9, wherein the volume-rendered images displayed in the gallery are automatically determined based on the selected appropriate protocol.

12. The method of claim 9, wherein the one or more visual controls are automatically determined by the selected appropriate protocol.

13. The method of claim 9, wherein the one or more visual controls are preset to a value determined by the selected appropriate protocol.

14. The method of claim 9, further comprising generating a report based on the volume-rendered image selected from the gallery.

15. A computer readable medium having computer executable instructions for performing a method for displaying a set of voxel data on a display device of a computer, the method comprising:

retrieving the set of voxel data;

selecting an appropriate protocol from a set of predefined protocols, said protocol being determined by at least one field in the set of voxel data, each of said predefined protocols defining a set of viewing characteristics to be applied to the set of voxel data;

displaying a gallery of volume-rendered images of the set of voxel data, each of said volume-rendered images displayed on the display device in accordance with the selected appropriate protocol; and displaying one or more visual controls operative to modify a volume-rendered image selected from the gallery.

16. The computer readable medium of claim 15, wherein the set of viewing characteristics includes one or more attributes selected from the group consisting of: contrast, transparency, and color.

17. The computer readable medium of claim 15, wherein the volume-rendered images displayed in the gallery are automatically determined based on the selected appropriate protocol.

18. The computer readable medium of claim 15, wherein the one or more visual controls are automatically determined by the selected appropriate protocol.

19. The computer readable medium of claim 15, wherein the one or more visual controls are preset to a value determined by the selected appropriate protocol.

20. The computer readable medium of claim 15, further having computer executable instructions for generating a report based on the volume-rendered image selected from the gallery.

* * * * *